US009233171B2

(12) United States Patent
Setiady et al.

(10) Patent No.: US 9,233,171 B2
(45) Date of Patent: Jan. 12, 2016

(54) METHOD OF TREATMENT OF TUMORS THAT ARE RESISTANT TO EGFR ANTIBODY THERAPIES BY EGFR ANTIBODY CYTOTOXIC AGENT CONJUGATE

(71) Applicants: Julianto Setiady, Waltham, MA (US); Peter U. Park, Somerville, MA (US); Thomas Chittenden, Sudbury, MA (US)

(72) Inventors: Julianto Setiady, Waltham, MA (US); Peter U. Park, Somerville, MA (US); Thomas Chittenden, Sudbury, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 13/682,948

(22) Filed: Nov. 21, 2012

(65) Prior Publication Data

US 2013/0156796 A1 Jun. 20, 2013

Related U.S. Application Data

(60) Provisional application No. 61/562,157, filed on Nov. 21, 2011, provisional application No. 61/639,452, filed on Apr. 27, 2012.

(51) Int. Cl.

| A61K 39/395 | (2006.01) |
| A61K 31/395 | (2006.01) |
| C07K 16/30 | (2006.01) |
| A61K 47/48 | (2006.01) |
| C07K 16/28 | (2006.01) |
| A61K 39/00 | (2006.01) |

(52) U.S. Cl.
CPC ..... *A61K 47/48369* (2013.01); *A61K 39/39558* (2013.01); *A61K 47/48384* (2013.01); *A61K 47/48569* (2013.01); *C07K 16/2863* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| 4,256,746 A | 3/1981 | Miyashita et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |

(Continued)

FOREIGN PATENT DOCUMENTS

| EP | 1 033 406 A1 | 9/2000 |
| EP | 2 457 586 A1 | 5/2012 |

(Continued)

OTHER PUBLICATIONS

Bianco et al., Intrinsic and acquired resistance to EGFR inhibitors in human cancer therapy, Endorine-Related Cancer, 12:S159-S171, 2005.*

(Continued)

*Primary Examiner* — Claire Kaufman
(74) *Attorney, Agent, or Firm* — Sterne, Kessler, Goldstein & Fox PLLC

(57) ABSTRACT

The present invention relates to the identification that EGFR antibody immunoconjugates are effective in inhibiting the growth of tumor cells that have developed EGFR and/or ALK resistance mechanisms. Methods of administering the EGFR antibody immunoconjugates to patients having resistant tumor cells is also disclosed.

51 Claims, 13 Drawing Sheets

(56) References Cited

U.S. PATENT DOCUMENTS

| | | | |
|---|---|---|---|
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,563,304 A | 1/1986 | Carlsson et al. |
| 4,943,533 A | 7/1990 | Mendelsohn et al. |
| 5,208,020 A | 5/1993 | Chari et al. |
| 5,212,290 A | 5/1993 | Vogelstein et al. |
| 5,401,828 A | 3/1995 | Vogelstein et al. |
| 5,416,064 A | 5/1995 | Chari et al. |
| 5,459,061 A | 10/1995 | Sato et al. |
| 5,470,571 A | 11/1995 | Herlyn et al. |
| 5,475,092 A | 12/1995 | Chari et al. |
| 5,558,864 A | 9/1996 | Bendig et al. |
| 5,585,499 A | 12/1996 | Chari et al. |
| 5,710,010 A | 1/1998 | Vogelstein et al. |
| 5,731,168 A | 3/1998 | Carter et al. |
| 5,750,373 A | 5/1998 | Garrard et al. |
| 5,756,291 A | 5/1998 | Griffin et al. |
| 5,814,317 A | 9/1998 | Vogelstein et al. |
| 5,844,093 A | 12/1998 | Kettleborough et al. |
| 5,846,545 A | 12/1998 | Chari et al. |
| 5,891,996 A | 4/1999 | Mateo de Acosta del Rio et al. |
| 5,942,602 A | 8/1999 | Wels et al. |
| 5,981,725 A | 11/1999 | Vogelstein et al. |
| 6,127,126 A | 10/2000 | Vogelstein et al. |
| 6,129,915 A | 10/2000 | Wels et al. |
| 6,217,866 B1 | 4/2001 | Schlessinger et al. |
| 6,235,883 B1 | 5/2001 | Jakobovits et al. |
| 6,333,410 B1 | 12/2001 | Chari et al. |
| 6,441,163 B1 | 8/2002 | Chari et al. |
| 6,455,498 B1 | 9/2002 | Vogelstein et al. |
| 6,506,883 B2 | 1/2003 | Meteo de Acosta del Rio et al. |
| 6,716,821 B2 | 4/2004 | Zhao et al. |
| 6,979,726 B1 | 12/2005 | von Hoegen et al. |
| 7,097,840 B2 | 8/2006 | Erickson et al. |
| 7,129,332 B2* | 10/2006 | Pastan et al. |
| 7,132,511 B2 | 11/2006 | Carr et al. |
| 7,247,301 B2 | 7/2007 | van de Winkel et al. |
| 7,276,497 B2 | 10/2007 | Chari et al. |
| 7,303,749 B1 | 12/2007 | Chari |
| 7,368,565 B2 | 5/2008 | Chari et al. |
| 7,473,796 B2 | 1/2009 | Chari et al. |
| 7,479,543 B2 | 1/2009 | Tsuchiya et al. |
| 7,575,748 B1 | 8/2009 | Erickson et al. |
| 7,585,857 B2 | 9/2009 | Chari et al. |
| 7,589,180 B2 | 9/2009 | Old et al. |
| 7,595,378 B2 | 9/2009 | van de Winkel et al. |
| 7,598,350 B2 | 10/2009 | Liu et al. |
| 7,601,354 B2 | 10/2009 | Chari |
| 7,628,986 B2 | 12/2009 | Weber et al. |
| 7,736,644 B2 | 6/2010 | Weber et al. |
| 7,749,697 B2 | 7/2010 | Oleksiewicz et al. |
| 7,780,964 B2 | 8/2010 | Ellis et al. |
| 7,846,443 B2 | 12/2010 | Presta et al. |
| 7,887,805 B2 | 2/2011 | Pedersen et al. |
| 7,892,777 B2 | 2/2011 | Fisher et al. |
| 7,935,793 B2 | 5/2011 | Balasa et al. |
| 7,989,598 B2 | 8/2011 | Steeves et al. |
| 8,088,387 B2 | 1/2012 | Steeves et al. |
| 8,101,183 B2 | 1/2012 | Siadak et al. |
| 8,137,669 B2 | 3/2012 | Goldmakher et al. |
| 8,163,888 B2 | 4/2012 | Steeves et al. |
| 8,198,417 B2 | 6/2012 | Steeves et al. |
| 8,236,319 B2 | 8/2012 | Chari et al. |
| 8,337,856 B2 | 12/2012 | Blättler et al. |
| RE43,899 E | 1/2013 | Blättler et al. |
| 8,388,960 B2 | 3/2013 | Goldmakher et al. |
| 8,563,509 B2 | 10/2013 | Chari et al. |
| 8,613,930 B2 | 12/2013 | Chari et al. |
| RE44,704 E | 1/2014 | Chari et al. |
| 8,685,920 B2 | 4/2014 | Chari et al. |
| 8,790,649 B2* | 7/2014 | Setiady et al. |
| 2002/0001587 A1 | 1/2002 | Erickson et al. |
| 2004/0031072 A1 | 2/2004 | La Rosa et al. |
| 2004/0259942 A1 | 12/2004 | Shaw et al. |
| 2005/0107325 A1 | 5/2005 | Manoharan et al. |
| 2005/0169933 A1 | 8/2005 | Steeves et al. |
| 2006/0147959 A1 | 7/2006 | Bell et al. |
| 2006/0233814 A1 | 10/2006 | Goldmakher et al. |
| 2007/0009972 A1 | 1/2007 | Chao et al. |
| 2007/0213292 A1 | 9/2007 | Stoffel et al. |
| 2008/0027130 A1 | 1/2008 | Chari et al. |
| 2008/0171040 A1 | 7/2008 | Ebens, et al. |
| 2009/0155282 A1 | 6/2009 | Weber et al. |
| 2009/0156790 A1 | 6/2009 | Weber et al. |
| 2009/0175887 A1 | 7/2009 | Weber et al. |
| 2009/0240038 A1 | 9/2009 | Weber et al. |
| 2009/0252681 A1 | 10/2009 | Laeremans et al. |
| 2009/0258442 A1 | 10/2009 | Polakiewicz et al. |
| 2009/0269343 A1* | 10/2009 | Bigner et al. |
| 2010/0008929 A1 | 1/2010 | Van De Winkel et al. |
| 2010/0111979 A1 | 5/2010 | Weber et al. |
| 2010/0129314 A1 | 5/2010 | Singh et al. |
| 2010/0166744 A1* | 7/2010 | Wong |
| 2010/0190247 A1 | 7/2010 | Lazar et al. |
| 2011/0287036 A1 | 11/2011 | Matsumura et al. |
| 2012/0156217 A1 | 6/2012 | Setiady et al. |
| 2013/0108620 A1 | 5/2013 | Blättler et al. |
| 2013/0131322 A1 | 5/2013 | Kaneda et al. |
| 2014/0023662 A1 | 1/2014 | Setiady et al. |
| 2014/0099308 A1 | 4/2014 | Setiady et al. |

FOREIGN PATENT DOCUMENTS

| | | |
|---|---|---|
| WO | WO 2005/010151 A2 | 2/2005 |
| WO | WO 2009/134976 A1 | 11/2005 |
| WO | WO 2008/098145 A1 | 8/2008 |
| WO | WO 2009/030239 A1 | 3/2009 |
| WO | WO 2010/009124 A2 | 1/2010 |
| WO | WO 2010/022736 A2 | 3/2010 |
| WO | WO 2010/042904 A2 | 4/2010 |
| WO | WO 2010/055950 A1 | 5/2010 |
| WO | WO 2011/145629 A1 | 11/2011 |
| WO | WO 2012/058588 A2 | 5/2012 |
| WO | WO 2012/058592 A2 | 5/2012 |
| WO | WO 2013/078271 A1 | 5/2013 |

OTHER PUBLICATIONS

Kalinowski et al., Regulation of epidermal growth factor receptor signaling and erlotinib sensitivity in head and neck cancer cells by miR-7.PLoS One 7(10):e47067. doi: 10.1371/journal.pone. 004706724,Oct. 2012.* lnukai et al., Presence of epidermal growth factor receptor gene T790M mutation as a minor clone in non-small cell lung cancer, Cancer Res. 66:7854-7858, 2006.*

Phillips et al., Targeting HER2-positive breast cancer with trastuzumab-DM1, an antibody-cytotoxic drug conjugate, Canc. Res. 68(22):9280-9290, Nov. 15, 2008.*

Boehrer et al., Erlotinib exhibits antineoplastic off-target effects in AML and MDS: a preclinical study, Blood, 111(4):2170-2180, Feb. 15, 2008.*

Brand et al., Molecular mechanisms of resistance to the EGFR monoclonal antibody cetuximab, Cancer Biol. Therapy, 11(9):777-792, May 1, 2011.*

Wheeler et al., Mechanisms of acquired resistance to cetuximab: role fo HER (erbB3) family members, Oncogene 27(28):3944-3956, Jun. 26, 2008.* van Houdt et al., Oncogenic KRAS desensitizes colorectal tumor cells to epidermal growth factor receptor inhibition and activation, Neoplasia, 12(6):443-452, Jun. 2010.*

Kwak et al., Irreversible inhibotrs of the EGF receptor may circumvent acquired resistance to gefitinib, PNAS USA, 102(21):7665-7670, May 24, 2005.*

Bardelli, A., and Siena, S., "Molecular Mechanisms of Resistance to Cetuximab and Panitumumab in Colorectal Cancer," *J. Clin. Oncol.* 28(7):1254-1261, American Society of Clinical Oncology, United States (Mar. 2010).

(56) References Cited

OTHER PUBLICATIONS

Baselga, J., and Arteaga, C.L., "Critical Update and Emerging Trends in Epidermal Growth Factor Receptor Targeting in Cancer," *J Clin. Oncol.* 23(11):2445-2459, American Society of Clinical Oncology, United States (Apr. 2005).

DeRoock, W., et al., "Effects of *KRAS, BRAF, NRAS*, and *PIK3CA* mutations on the efficacy of cetuximab plus chemotherapy in chemotherapy-refractory metastatic colorectal cancer: a retrospective consortium analysis," *Lancet Oncol.* 11:753-762, Lancet Pub. Group, England (Aug. 2010).

Gill, G.N., et al., "Monoclonal Anti-epidermal Growth Factor Receptor Antibodies Are Inhibitors of Epidermal Growth Factor Binding and Antagonists of Epidermal Growth Factor-stimulated Tyrosine Protein Kinase Activity," *J. Biol. Chem.* 259(12):7755-7760, American Society for Biochemistry and Molecular Biology, England (Jun. 1984).

Goldstein, N.I., et al., "Biological Efficacy of a Chimeric Antibody to the Epidermal Growth Factor Receptor in a Human Tumor Xenograft Model," *Clin. Cancer Res.* 1:1311-1318, American Association for Cancer Research, United States (Nov. 1995).

Li, T., and Perez-Soler, R., "Skin toxicities associated with epidermal growth factor receptor inhibitors," *Targ. Oncol.* 4:107-119, Springer-Verlag, France (2009).

Linardou, H., et al., "Somatic *EGFR* mutations and efficacy of tyrosine kinase inhibitors in NSCLC," *Nat. Rev. Clin. Oncol.* 6:352-366, Macmillian Publishers Limited, England (Jun. 2009).

Paz-Ares, L., et al., "Clinical outcomes in non-small-cell lung cancer patients with EGFR mutations: pooled analysis," *J. Cell. Mol. Med.* 14(1-2):51-69, F. Hoffmann—La Roche Ltd., Switzerland (2010).

Prewett, M., et al., "Mouse-Human Chimeric Anti-Epidermal Growth Factor Receptor Antibody C225 Inhibits the Growth of Human Renal Cell Carcinoma Xenografts in Nude Mice," *Clin. Cancer Res.* 4:2957-2966, American Association for Cancer Research, United States (Dec. 1998).

Stoll, S.W., et al., "EGF receptor signaling inhibits keratinocyte apoptosis: evidence for mediation by Bcl-$X_L$," *Oncogene* 16:1493-1499, Stockton Press, United Kingdom (Mar. 1998).

Widdison, W.C., et al. "Semisynthetic Maytansine Analogues for the Targeted Treatment of Cancer," *J. Med. Chem.* 49:4392-4408, American Chemical Society, United States (2006).

Baselga, J., "Why the Epidermal Growth Factor Receptor? The Rationale for Cancer Therapy," *The Oncologist* 7(suppl 4):2-8, AlphaMed Press, United States (2002).

Carlsson, J., et al, "Protein Thiolation and Reversible Protein-Protein Conjugation," *Biochem. J.* 173:723-737, Portland Press, England (1978).

Friess, T., et al., "Combination Treatment with Erlotinib and Pertuzumab against Human Tumor Xenografts is Superior to Monotherapy," *Clin Cancer Res* 11(14):5300-5309, American Association for Cancer Research, United States (2005).

Hashida, S., et al., "More Useful Maleimide Compounds for the Conjugation of Fab' to Horseradish Peroxidase through Thiol Groups in the Hinge," *Journal of Applied Biochemistry* 6:56-63, Academic Press Inc., United States (1984).

Jost, M., et al., "Matrix-independent Survival of Human Keratinocytes through an EGF Receptor/MAPK-Kinase-dependent Pathway," *Molecular Biology of the Cell* 12:1519-1527, The American Society for Cell Biology, United States (2001).

Kamat, V., et al., "Enhanced EGFR inhibition and distinct epitope recognition by EGFR antagonistic mAbs C225 and 425," *Cancer Biology & Therapy* 7(5):726-733, Landes Bioscience, United States (2008).

Kim, S., et al., "E-cadherin promotes EGFR-mediated cell differentiation and MUC5AC mucin expression in cultured human airway epithelial cells," *Am J Physiol Lung Cell Mol Physiol* 289:L1049-L1060, the American Physiological Society, United States (2005).

Kimura, H., et al., "Antibody-dependent cellular cytotoxicity of cetuximab against tumor cells with wild-type or mutant epidermal growth factor receptor," *Cancer Sci* 98(8):1275-1280, Japanese Cancer Association, Japan (2007).

Lammerts van Bueren, J.L., et al., "The antibody zalutumumab inhibits epidermal growth factor receptor signaling by limiting intra- and intermolecular flexibility," *PNAS* 105(16):6109-6114, The Nathional Academy of Sciences of the USA, United States (2008).

Laux, I., et al., "Epidermal growth factor receptor dimerization status determines skin toxicity to HER-kinase targeted therapies," *British Journal of Cancer* 94:85-92, Cancer Research UK, England (2006).

Liu, F-T, et al., "New Procedures for Preparation and isolation of Conjugates of Proteins and a Synthetic Copolymer of D-Amino Acids and Immunochemical Characterization of such Conjugates," *Biochemistry* 18:690-697, American Chemical Society, United States (1979).

Modjtahedi, H., et al., "Anti-EGFR Monoclonal Antibodies which Act as EGF, TGFα HB-EGF and BTC Antagonists Block the Binding of Epiregulin to EGFR-Expressing Tumours," *Int. J. Cancer* 75:310-316, Wiley-Liss, Inc., United States (1998).

Mok, T., et al., "A Small Step Towards Personalized Medicine for Non-small Cell Lung Cancer," *Discovery Medicine* 8(43):227-231, Discovery Medicine, United States (2009).

Mutsaers, A.J., et al., "Dose-Dependent Increases in Circulating TGF-α and Other EGFR Ligands Act as Pharmacodynamic Markers for Optimal Biological Dosing of Cetuximab and are Tumor Independent," *Clin Cancer Res* 15(7):2397-2405, American Association for Cancer Research, United States (2009).

Nygren, P-A., "Alternative binding proteins: Affibody binding proteins developed from a small three-helix bundle scaffold," *FEBS Journal* 275:2668-2676, The Author Journal compilation, FEBS, England (2008).

Ocvirk, J, "Management of cetuximab-induced skin toxicity with the prophylactic use of topical vitamin K1 cream," *Radiol Oncol* 44(4):256-266, Versita, Slovenia (2010).

Raben, D., et al., "The Effects of Cetuximab Alone and in Combination with Radiation and/or Chemotherapy in Lung Cancer," *Clinical Cancer Research* 11:795-805, American Association for Cancer Research, United States (2005).

Shalaby, M.R., et al., "Development of Humanized Bispecific Antibodies Reactive with Cytotoxic Lymphocytes and Tumor Cells Overexpressing the HER2 Protooncogene," *J. Exp. Med.* 175:217-225, The Rockefeller University Press, United States (1992).

Sheets, M.D., et al., "Efficient construction of a large nonimmune phage antibody library: The Production of high-affinity human single-chain antibodies to protein antigens," *Proc. Natl. Acad. Sci. USA* 95:6157-6162, The National Academy of Sciences, United States (1998).

Steiner, P., et al., "Tumor Growth Inhibition with Cetuximab and Chemotherapy in Non-Small Cell Lung Cancer Xenografts Expressing Wild-type and Mutated Epidermal Growth Factor Receptor," *Clin Cancer Res* 13(5):1540-1551, American Association for Cancer Research, United States (2007).

Ullrich, A., et al., "Human epidermal growth factor receptor cDNA sequence and aberrant expression of the amplified gene in A431 epidermoid carcinoma cells," *Nature* 309:418-425, Nature Publishing Group, England (1984).

Yang, X-D, et al., "Eradication of Established Tumors by a Fully Human Monoclonal Antibody to the Epidermal Growth Factor Receptor without Concomitant Chemotherapy," *Cancer Research* 59:12236-1243, American Association for Cancer Research, United States (1999).

Yarden, Y., and Sliwkowski, M.X., "Untangling the ErbB Signalling Network," *Nature Reviews Molecular Cell Biology* 2:127-137, Macmillan Magazines Ltd, England (2001).

Yoshitake, S., et al., "Conjugation of Glucose Oxidase from *Aspergillus niger* and Rabbit Antibodies Using N-Hydroxysuccinimide Ester of *N*-(4-Carboxycyclohexylmethyl)-Maleimide," *Eur. J. Biochem.* 101:395-399, Blackwell Science Ltd., England (1979).

NCBI Entrex, GenBank Report, Accession No. AY208307.1, Zhang, J.Q., and Davidson, W.F., Entry Date Mar. 2004.

NCBI Entrex, GenBank Report, Accession No. M15225.1, Chua, M.M., et al., Entry Date Apr. 1993.

"UniProt_B4NGM2, GK21222," UniProt.com, accessed at http://www.uniprot.org/uniprot/B4NGM2, accessed on Dec. 5, 2012, 3 pages.

(56) References Cited

OTHER PUBLICATIONS

International Search Report for International Application No. PCT/US11/58378, European Patent Office, Netherlands, mailed on Jun. 8, 2012.
Sasaki, T., et al., "A Novel ALK Secondary Mutation and EGFR Signaling Cause Resistance to ALK Kinase Inhibitors," *Cancer Res* 71(18):6051-6060, American Association for Cancer Research, United States (2011).
International Search Report for International Application No. PCT/US12/66205, U.S. Patent Office, United States, mailed on Feb. 26, 2013.
Lamminmaki, U., et al., "Crystal Structure of a recombinant anti-estradiol Fab fragment in complex with 17beta-estradiol," *J. Biol. Chem.* 276(39): 36687-36694, American Society for Biochemistry and Molecular Biology, United States (2001).
Li, S., et al., "Structural basis for inhibition of the epidermal growth factor receptor by cetuximab," *Cancer Cell* 7:301-311, Cambridge, United States (2005).
MacCallum, R.M., et al., "Antibody—antigen Interactions: Contact Analysis and Binding Site Topography," *J. Mol. Biol.* 262:732-745, Elsevier, England (1996).
Rudikoff, S., et al., "Single amino acid substitution altering antigen-binding specificity," *Proc. Natl. Acad. Sci. USA* 7: 1979-1983, National Academy of the Sciences, United States (1982).
Office Action mailed on Mar. 18, 2013 in U.S. Appl. No. 13/284,398, inventors Setiady et al., filed Oct. 28, 2011.
Ramakrishnan, M.S., et al., "Nimotuzumab, a promising therapeutic monoclonal for treatment of tumors of epithelial origin," *mAbs* 1(1):41-48, Landes Bioscience, United States (2009).
Skartved, N.J.O., et al., "Preclinical pharmacokinetics and safety of Sym0004: A synergistic antibody mixture directed against epidermal growth factor receptor," Clin. Cancer Res. 17:5962-5972, American Association for Cancer Research, United States (2011).
Takeda, M., et al., "Nimotuzumab, a novel monoclonal antibody to the epidermal growth factor receptor, in the treatment of non-small cell lung cancer," *Lung Cancer: Targets and Therapy* 2:59-67, Dove Medical Press Ltd., United Kingdom (2011).
Willmarth, N.E., et al., "Autocrine and Juxtacrine Effects of Amphiregulin on the Proliferative, Invasive, and Migratory Properties of Normal and Neoplastic Human Mammary Epithelial Cells," *J. Biol. Chem.* 281:37728-37737, The American Society for Biochemistry and Molecular Biology, Inc., United States (2006).
International Preliminary Report on Patentability for International Application No. PCT/US2011/058385, U.S. Patent Office, United States, mailed May 10, 2013.
International Preliminary Report on Patentability for International Application NO. PCT/US2011/058378, U.S. Patent Office, United States, mailed May 10, 2013.
Office Action mailed on Aug. 12, 2013 in U.S. Appl. No. 13/284,398, inventors Setiady et al., filed Oct. 28, 2011.
Castro-Carpeño, J. d., et al., "Treatment for ALK-mutated non-small-cell lung cancer: a new miracle in the research race," *Clin Transl Oncol* 13:774-779, Springer, Germany (Nov. 2011).
Karapetis, C. S., et al., "*K-ras* Mutations and Benefit from Cetuximab in Advanced Colorectal Cancer," *The New England Journal of Medicine* 359(17):1757-1765, Massachusetts Medical Society, United States (2008).
Kataoka, Y., et al., "Association between gain-of-function mutations in *PIK3CA* and resistance to HER2-targeted agents in *HER2*-amplified breast cancer cell lines," *Annals of Oncology* 21:255-262, Oxford University, United Kingdom (Feb. 2010).
Koivunen, J. P., et al., "EML4-ALK fusion gene and efficacy of an ALK kinase inhibitor in lung cancer," *Clin Cancer Res*. 14(13):4275-4283, American Association for Cancer Research, United States (2008).
Lee, J. Y., et al., "PI3K Charges Ahead," *Science* 317:206-207, American Association for the Advancement of Science, United States (2007).
Li, D., et al., "Therapeutic anti-EGFR antibody 806 generates responses in murine de novo EGFR mutant-dependent lung carcinomas," *J. Clin. Invest* 117(2):346-352, American Society for Clinical Investigation, United States (2007).
Rebucci, M., et al., "Mechanisms underlying resistance to cetuximab in the HNSCC cell line: Role of AKT inhibition in bypassing this resistance," *International Journal of Oncology* 38:189-200, Spandidos Publications, Greece (Jan. 2011).
Sequist, L. V., et al., "Genotypic and Histological Evolution of Lung Cancers Acquiring Resistance to EGFR Inhibitors," *Sci Transl Med.* 3(75):75ra26, American Association for the Advancement of Science, United States (Mar. 2011).
Sok, J. C., et al., "Mutant Epidermal Growth Factor Receptor (EGFRvIII) Contributes to Head and Neck Cancer Growth and Resistance to EGFR Targeting," *Clin Cancer Res* 12:5064-5073, American Association for Cancer Research (2006).
Suda, K., et al., "Reciprocal and Complementary Role of *MET* Amplification and *EGFR* T790M Mutation in Acquired Resistance to Kinase Inhibitors in Lung Cancer," *Clin Cancer Res* 16:5489-54998, American Association for Cancer Research, United States (Nov. 2010).
Uramoto, H., et al., "Expression of selected gene for acquired drug resistance to EGFR-TKI in lung adenocarcinoma," *Lung Cancer* 73:361-365, Elsevier Ireland Ltd., Ireland (Sep. 2011).
Yano, S., et al., "Hepatocyte Growth Factor Induces Gefitinib Resistance of Lung Adenocarcinoma with Epidermal Growth Factor Receptor-Activating Mutations," *Cancer Res* 68:9479-9487, American Association for Cancer Research, United States (2008).
Yauch, R. L., et al., "Epithelial versus Mesenchymal Phenotype Determines in vitro Sensitivity and Predicts Clinical Activity of Erlotinib in Lung Cancer Patients," *Clin Cancer Res* 11:8686-8698, American Association for Cancer Research, United States (2005).
Akashi, Y., et al., "Enhancement of the antitumor activity of ionising radiation by nimotuzumab, a humanised monoclonal antibody to the epidermal growth factor receptor, in non-small cell lung cancer lines of differing epidermal growth factor receptor status," *British Journal of Cancer* 98:749-755, Cancer Research UK, United Kingdom (2008).
Clarke, J., et al., "Duration of chronic toxicity studies for biotechnology-derived pharmaceuticals: Is 6 months still appropriate?" *Regulatory Toxicology and Pharmacology* 50:2-22, Elsevier Inc., United States (2008).
Talavera, A., et al., "Nimotuzumab, an Antitumor Antibody that Targets the Epidermal Growth Factor Receptor, Blocks Ligand Binding while Permitting the Active Receptor Conformation," *Cancer Res* 67(14):5851-5859, American Association for Cancer Research, United States (2009).
Eurasian Search Report, completed Nov. 25, 2013, in Eurasian Application No. 201390472, Moscow, Russia.
Notice of Allowance, mailed on Nov. 21, 2013, U.S. Appl. No. 13/284,398, inventors Setiady et al., filed Oct. 28, 2011.
Corrected Notice of Allowance, mailed on Feb. 18, 2014, in U.S. Appl. No. 13/284,398, inventors Setiady et al., filed Oct. 28, 2011.
Guo, L., et al., "Studies of Ligand-Induced Site-Specific Phosphorylation of Epidermal Growth Factor Receptor," *J Am Soc Mass Spectrom* 14:1022-1031, American Society for Mass Spectrometry, United States (2003).
Kovtun, Y.V., et al., "Antibody-Maytansinoid Conjugates Designed to Bypass Multidrug Resistance," *Cancer Research* 70(6):2528-2537, American Association for Cancer Research, United States (2010).
Maloney, E.M., et al., "Designing Potent Antibody-Maytansinoid Conjugated (AMCs): The Impact of Lysosomal Processing Efficient and Conjugate Linker Selection on Anticancer Activity," 2009 AACR-NCI-EORTC International Conference on Molecular Targets and Cancer Therapeutics, Boston, MA (Nov. 15-19, 2009) Abstract #B120 Poster, American Association for Cancer Research, United States (Nov. 15, 2009).
Ojima, I., et al., "Tumor-Specific Novel Taxoid—Monoclonal Antibody Conjugates," *Journal of Medicinal Chemistry* 45(26):5620-5623, American Chemical Society, United States (2002).
Ojima, I., "Guided Molecular Missiles for Tumor-Targeting Chemotherapy—Case Studies Using the Second Generation Taxoids as Warheads," *Accounts of chemical research* 41(1):108-119, American Chemical Society, United States (2008).

(56) References Cited

OTHER PUBLICATIONS

Schmiedel, J., et al., "Metuzumab binding to EGFR prevents the conformational rearrangement required for dimerization," *Cancer Cell* 13(4):365-373, Cell Press, United States (2008).

Singh, R., and Maloney, E.K.. "Labeling of Antibodies by in Situ Modification of Thiol Groups Generated from Selenol-Catalyzed Reduction of Native Disulfide Bonds," *Analytical Biochemistry* 304(2):147-156, Academic Press, United States (2002).

Singh, R. and Erickson, H.K., "Antibody-Cytotoxic Agent Conjugates: Preparation and Characterization," in *Therapeutic Antibodies: Methods and Protocols*, Dimitrov, A.S., Ed., Chapter 23, pp. 445-467, Humana Press, United States (2009).

Wu, X., and Ojima, I., "Tumor Specific Novel Taxoid-Monoclonal Antibody Conjugates," *Current Medicinal Chemistry* 11(4):429-438. Bentham Science Publishers Ltd., Netherlands (2004).

Eurasian Search Report, completed Feb. 7, 2014, in Eurasian Application No. 201390575, Moscow, Russia.

Maloney, E., et al.,"Designing Potent Antibody-Drug Conjugates (ADCs): The Impact of Lysosomal Processing Efficiency and Conjugate Linker Selection on Anticancer Activity," 2009 AACR-NCI-EORTC International Conference on Molecular Targets and Cancer Therapeutics, Boston, MA (Nov. 15-19, 2009) Abstract #B120, American Association for Cancer Research, United States (submitted electronically on Sep. 9, 2009).

Unpublished U.S. Appl. No. 14/032,046, filed Sep. 19, 2013, now US 2014/0212411.

International Search Report for International Application No. PCT/US11/58385, ISA/US, Alexandria, Virginia, United States, mailed Jun. 21, 2012.

Brown, M., et al., "Tolerance to a Single, but Not Multiple, Amino Acid Replacements in Antibody $V_H$ CDR2: A Means of Minimizing B Cell Wastage from Somatic Hypermutation?" *The Journal of Immunology* 156(9):3285-3291, The American Association of Immunologists, Inc., United States (1996).

Fakih, M. and Vincent, M., "Adverse events associated with anti-EGFR therapies for the treatment of metastatic colorectal cancer," *Current Oncology* 17(Suppl. 1):S18-S30, Multimed, Canada (Jul. 2010).

Milenic, D.E., et al., "Cetuximab: Preclinical Evaluation of a Monoclonal Antibody Targeting EGFR for Radioimmunodiagnostics and Radioimmunotherapeutic Applications," *Cancer Biotherapy & Radiopharmaceuticals* 23(5):619-632, Mary Ann Liebert, Inc., United States (2008).

Winkler, K., et al., "Changing the Antigen Binding Specificity by Single Point Mutations of an Anti-p24 (HIV-1) Antibody," *The Journal of Immunology* 165(8):4505-4514, The American Association of Immunologists, Inc., United States (2000).

Supplementary European Search Report and European Search Opinion for European Application No. EP 11837192, European Patent Office, Germany, mailed on Sep. 19, 2014.

Office Action mailed Oct. 23, 2014, in U.S. Appl. No. 13/800,624, Setiady, J., et al., filed Mar. 13, 2013.

Extended European Search Report for EP Application No. EP 11 83 7196, European Patent Office, The Hague, mailed on Feb. 13, 2015.

Burris, H. A., "Trastuzumab Emtansine: A Novel Antibody-Drug Conjugate For Her2-Positive Breast Cancer," *Expert Opinion On Biological Therapy* 11(6): 807-819, Informa UK Ltd., England (Jun. 2011).

Li H. et al, "Genomic Analysis of Head and Neck Squamous Cell Carcinoma Cell Lines and Human Tumors: A Rational Approach to Preclinical Model Selection," Molecular Cancer Research 12(4): 571-582, American Association for Cancer Research, United States (Apr. 2014).

Ponte J. F., et. al, "Preclinical Evaluation Of IMGN289, An Anti-EGFR Antibody-Maytansinoid Conjugate For The Treatment Of Squamous Cell Carcinoma Of The Head And Neck," Proceedings: AACR 104th Annual Meeting 2013, *Cancer Research* 73(8 Suppl):Abstract No. 3483, American Association for Cancer Research, United States (Apr. 2013), Accessed at http://cancerres.aacrjournals.org/content/73/8_Supplement/5483.short, on Oct. 14, 2015.

Extended European Search Report and Written Opinion for European Application No. EP 12 85 0911, European Patent office, Germany, Mailed on Sep. 18, 2015, pp. 1-10.

\* cited by examiner

Figure 1. NCI-H1975
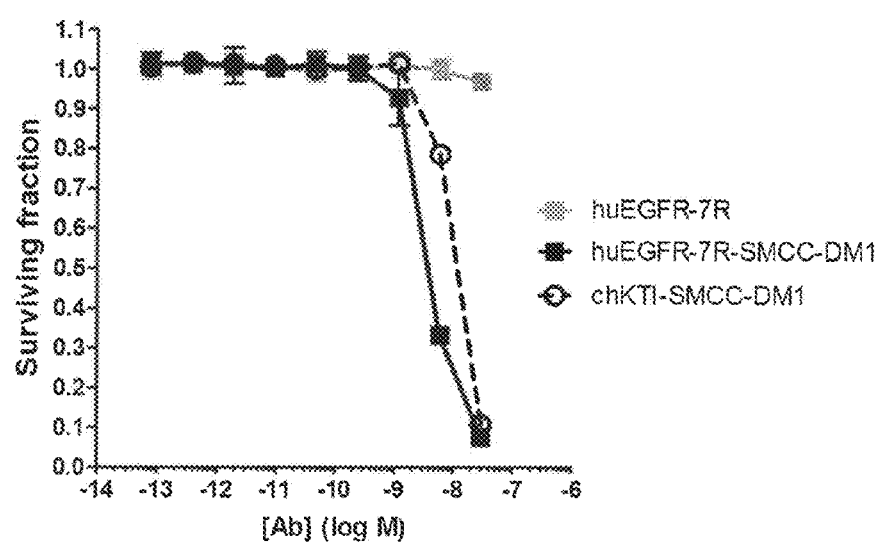

Figure 2. HCC827
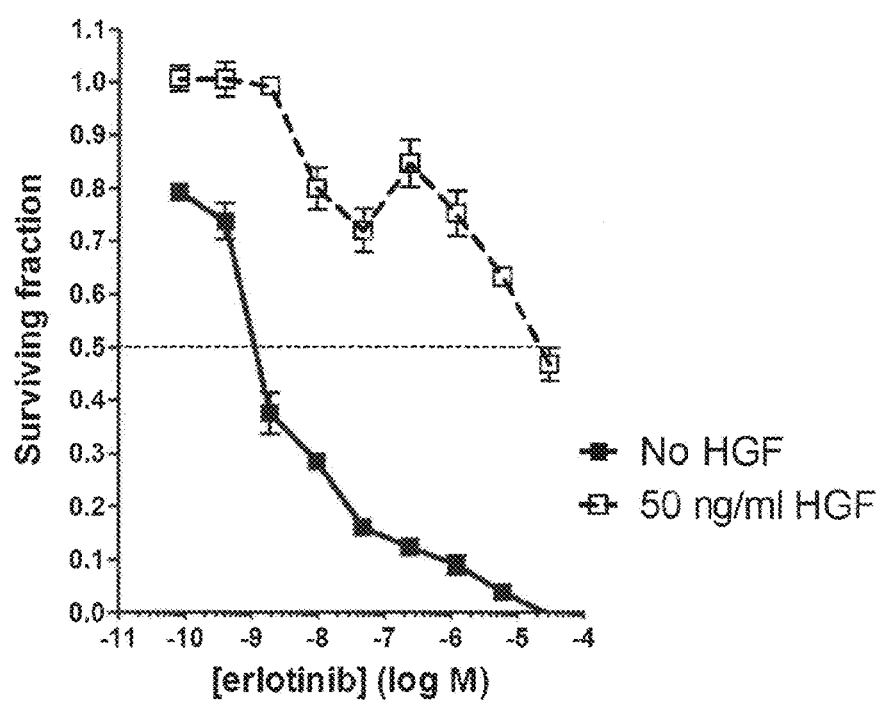

Figure 3. HCC827
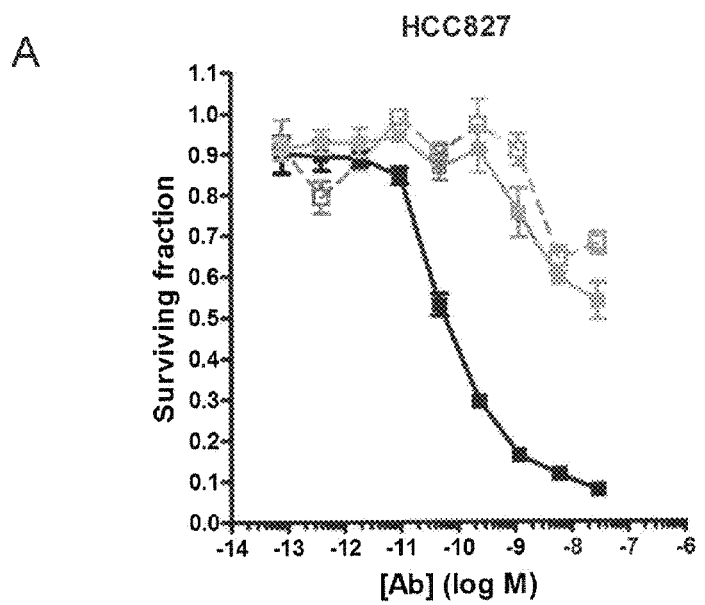
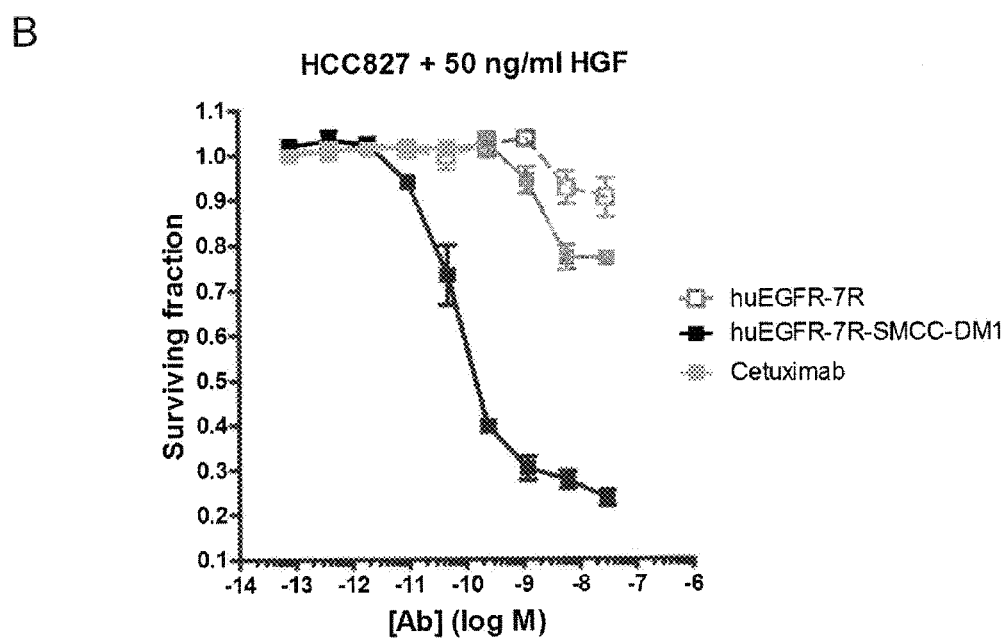

Figure 4. H226
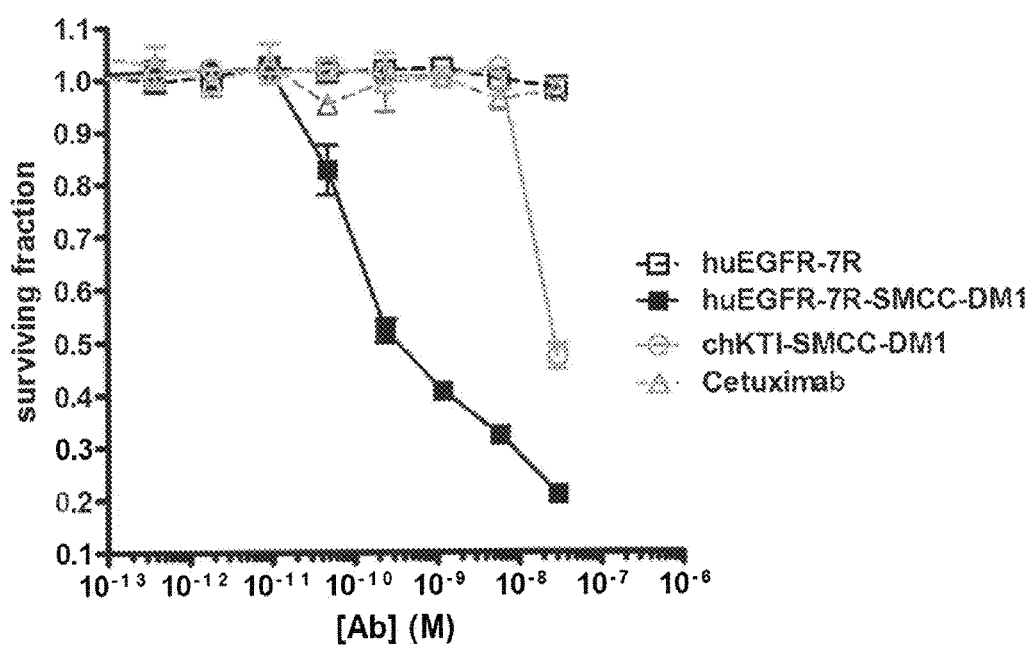

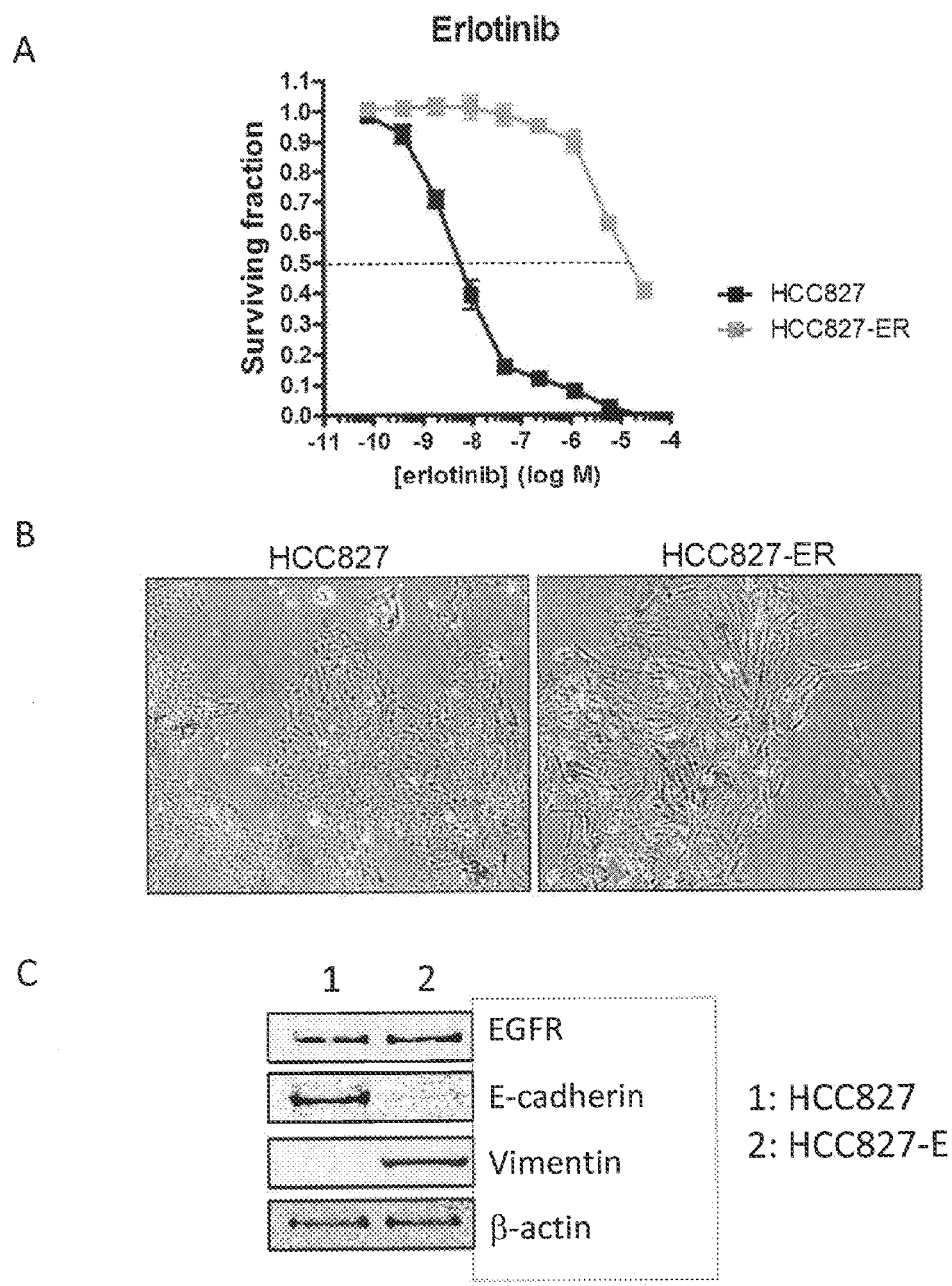

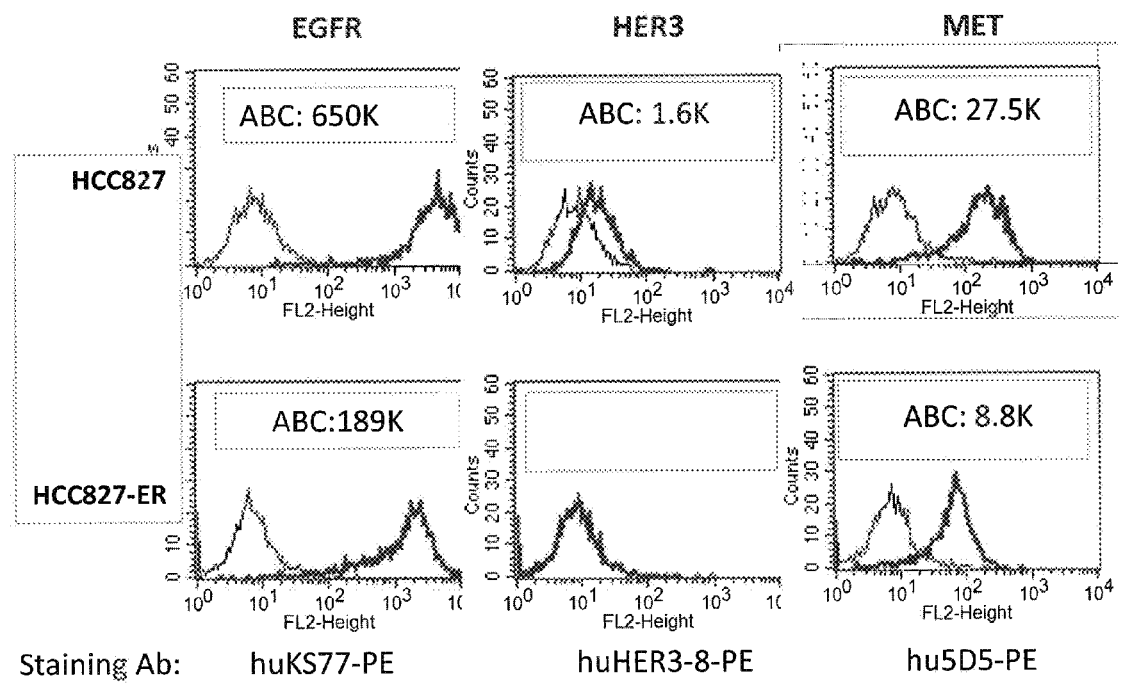
Figure 6. HCC827-ER

Figure 7. HCC827-ER
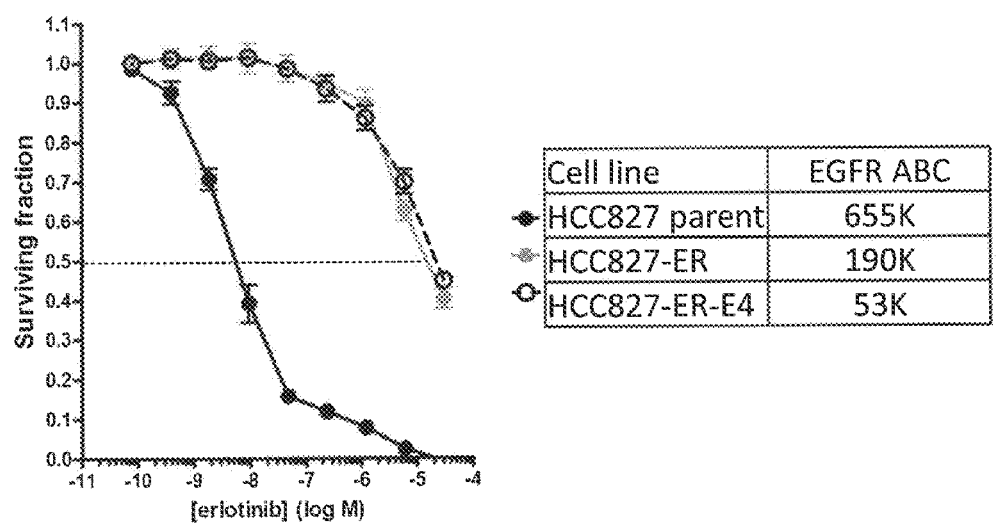

Figure 8. HCC827-ER
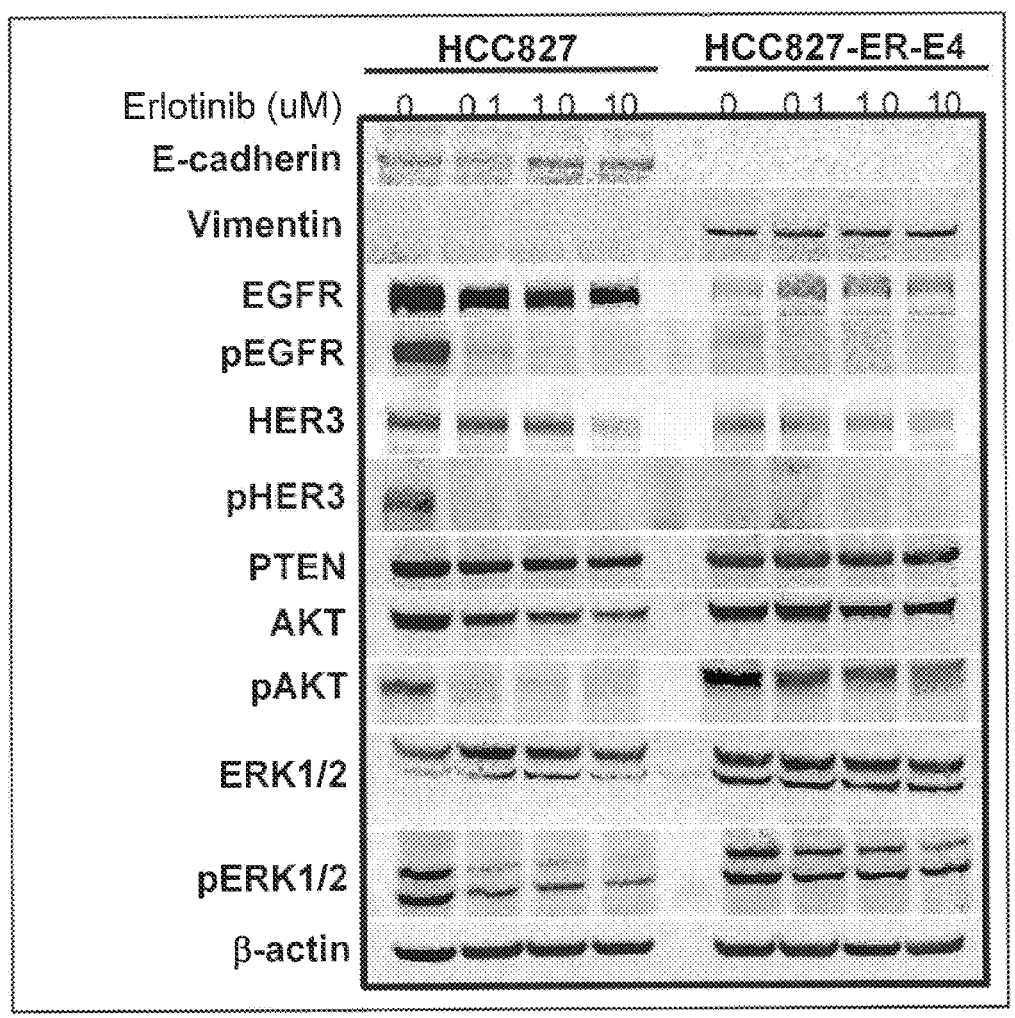

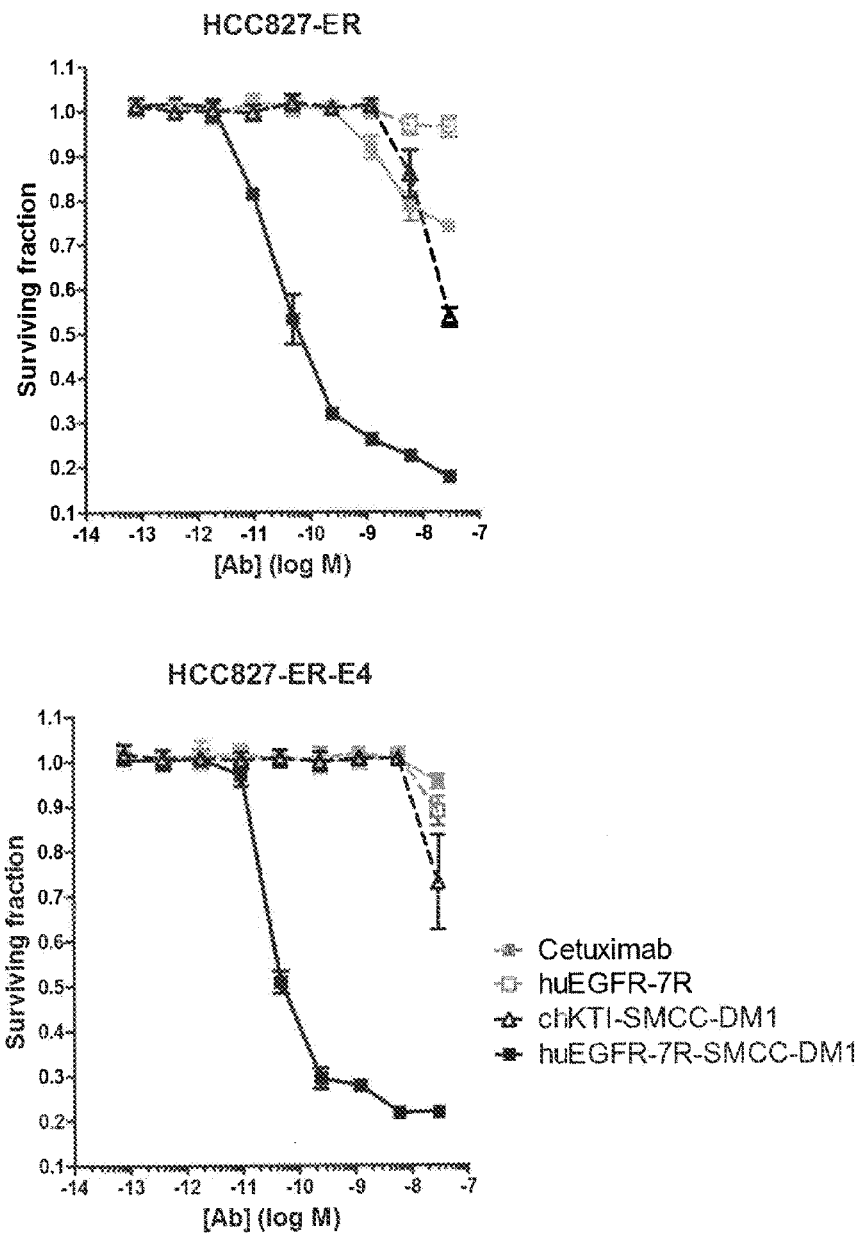

Figure 10. SW620
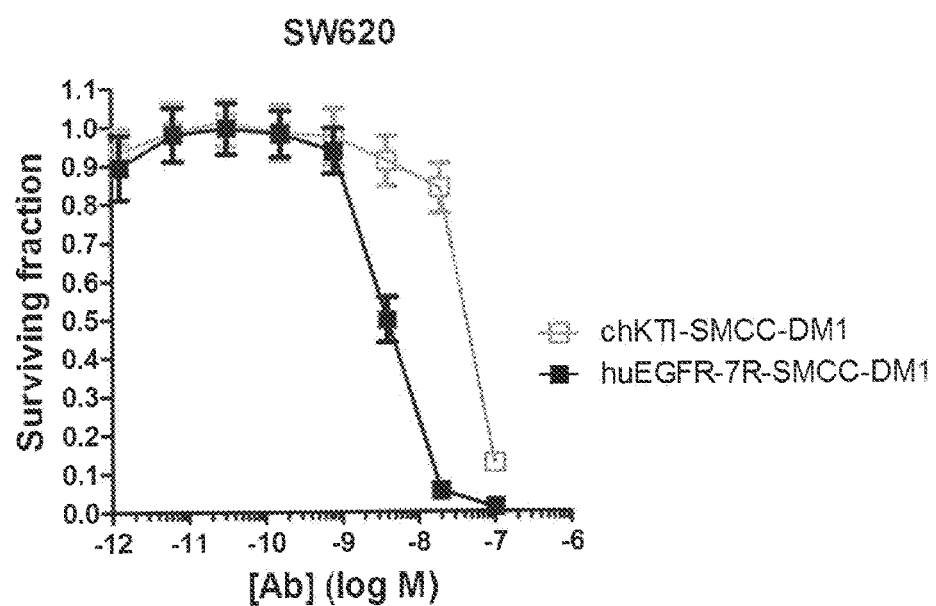

Figure 11. Detroit562
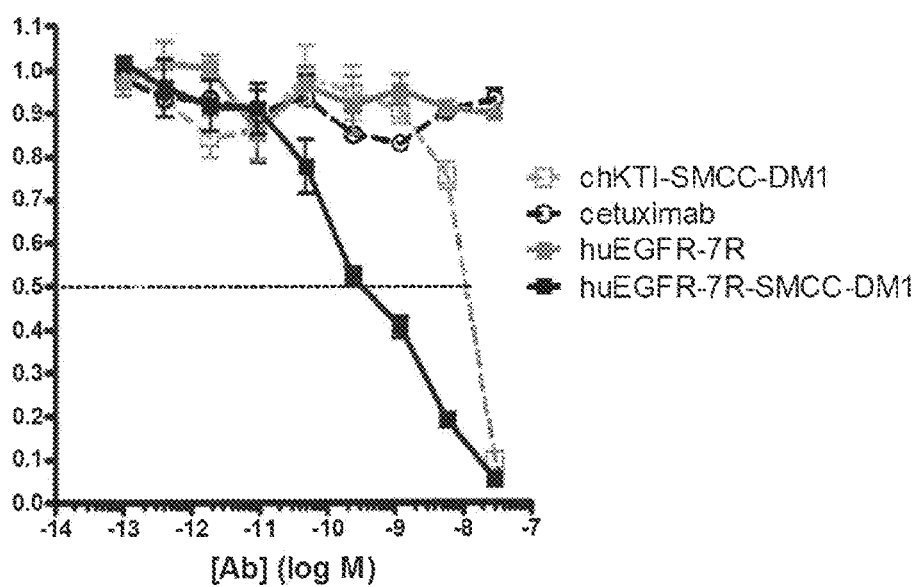

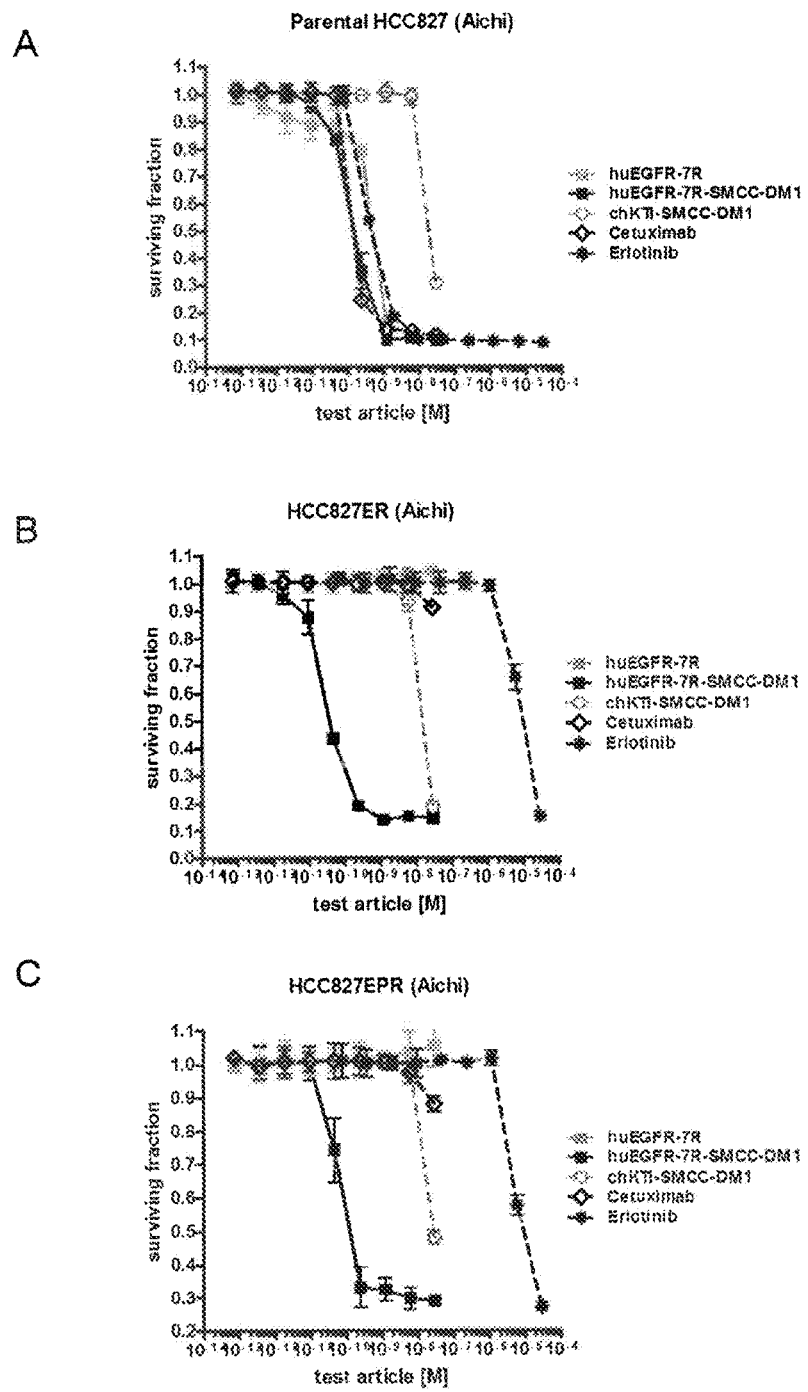
Figure 12. HCC827, ER and EPR (Aichi)

Figure 13. H2228
A
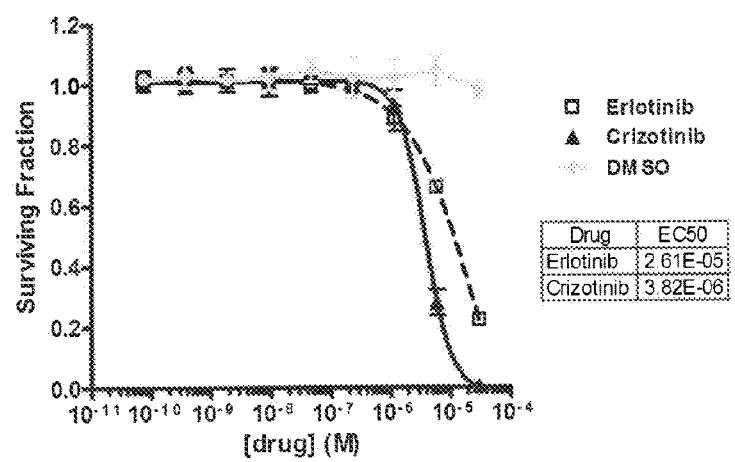
B
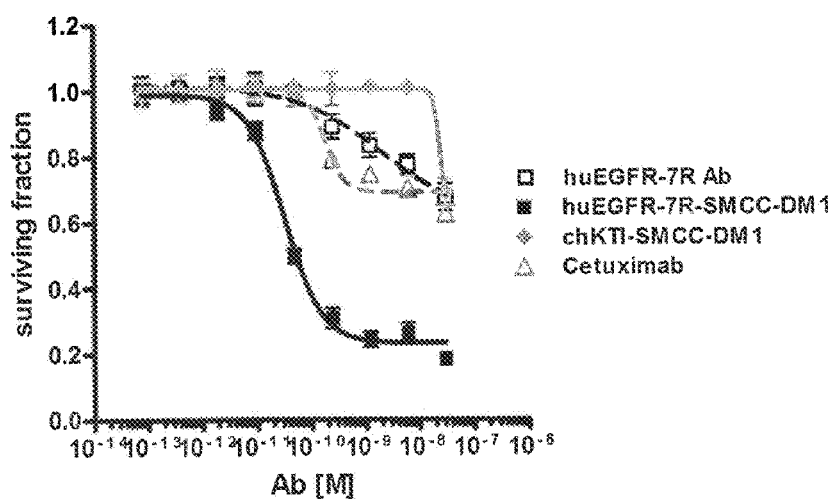

```
SEQUENCE LISTING

<160> NUMBER OF SEQ ID NOS: 3

<210> SEQ ID NO 1
<211> LENGTH: 119
<212> TYPE: PRT
<213> ORGANISM: Artificial Sequence
<220> FEATURE:
<223> OTHER INFORMATION: huEGFR-7R VH

<400> SEQUENCE: 1

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Thr Tyr Thr Gln Lys Phe
    50                  55                  60

Gln Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser
        115

<210> SEQ ID NO 2
<211> LENGTH: 108
<212> TYPE: PRT
<213> ORGANISM: Artificial Sequence
<220> FEATURE:
<223> OTHER INFORMATION: huEGFR-7R VL v1.0

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Tyr Gln His Lys Pro Gly Lys Gly Pro Lys Leu Leu Ile
        35                  40                  45
```

```
                                   -continued

His Tyr Thr Ser Thr Leu His Pro Gly Ile Pro Ser Arg Phe Ser Gly
        50                  55                  60

Ser Gly Ser Gly Arg Asp Tyr Ser Phe Ser Ile Ser Ser Leu Glu Pro
 65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg
                100                 105

<210> SEQ ID NO 3
<211> LENGTH: 108
<212> TYPE: PRT
<213> ORGANISM: Artificial Sequence
<220> FEATURE:
<223> OTHER INFORMATION: huEGFR-7R VL v1.01

<400> SEQUENCE: 3

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Asn Tyr
                20                  25                  30

Leu Ala Trp Tyr Gln His Lys Pro Gly Lys Gly Pro Lys Leu Leu Ile
            35                  40                  45

His Tyr Thr Ser Thr Leu His Pro Gly Ile Pro Ser Arg Phe Ser Gly
        50                  55                  60

Ser Gly Ser Gly Arg Asp Tyr Ser Phe Ser Ile Ser Ser Leu Glu Pro
 65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg
                100                 105
```

METHOD OF TREATMENT OF TUMORS THAT ARE RESISTANT TO EGFR ANTIBODY THERAPIES BY EGFR ANTIBODY CYTOTOXIC AGENT CONJUGATE

CROSS-REFERENCE TO RELATED APPLICATIONS

This application claims the priority benefit of U.S. Provisional Application No. 61/562,157, filed Nov. 21, 2011, and U.S. Provisional Application No. 61/639,452, filed Apr. 27, 2012, each of which is hereby incorporated by reference herein in its entirety.

REFERENCE TO SEQUENCE LISTING SUBMITTED ELECTRONICALLY

The content of the electronically submitted sequence listing, file name 2921.0240002_SequenceListing.txt; size 3,585 bytes; and date of creation Aug. 25, 2014, filed herewith, is incorporated herein by reference in its entirety.

DESCRIPTION OF THE INVENTION

1. Field of the Invention

The present invention relates to the identification that EGFR antibody immunoconjugates are effective in inhibiting the growth of tumor cells that have developed EGFR resistance mechanisms.

2. Background of the Invention

The epidermal growth factor receptor (EGFR; ErbB-1; HER1) is the cell surface receptor for the epidermal growth factor (EGF) family of extracellular protein ligands (Herbst R S. Int J Radiat Oncol Bio Phys 59: 21 (2004)). EGFR is a member of the ErbB family of receptors, a subfamily of four closely related receptor tyrosine kinases: EGFR, HER2/c-neu (ErbB2), HER3 (ErbB-3) and HER4 (ErbB-4). EGFR activation is triggered by binding of its specific ligands such as epidermal growth factor (EGF) and transforming growth factor-α (TGFα). Upon ligand binding, EGFR undergoes a transition from an inactive monomeric form to an active homodimer. In addition, EGFR may pair with another member of the ErbB receptor family such as HER2 and HER3 to create an active heterodimer. EGFR dimerization stimulates its intrinsic intracellular protein tyrosine kinase activity that leads to autophosphorylation of several tyrosine residues in the carboxy-terminus (Downward J. et al., Nature 311: 483 (1984)). The autophosphorylation then elicits downstream signaling cascades, principally the MAPK, Akt and JNK pathways, leading to DNA synthesis and cell proliferation.

EGFR is an important oncogene. EGFR overexpression and mutations that lead to constitutive activation have been associated with a number of cancers, including lung cancer, colorectal cancer, head and neck cancer, and glioblastoma multiforme (Zhang H. et al., J Clin Invest 117: 2051 (2007)). This finding has led to the development of anti-cancer therapeutics directed against EGFR. Two small molecule tyrosine kinase inhibitors (TKIs), erlotinib (Tarceva) and gefitinib (Iressa), have been approved for non-small cell lung cancer (NSCLC) and pancreatic cancer. In addition, two antagonistic monoclonal antibodies against EGFR, cetuximab (Erbitux) and panitumumab (Vectibix) have been approved for squamous cell carcinoma of head and neck (SCCHN) and colorectal cancer (CRC).

The two EGFR kinase inhibitors, erlotinib and gefitinib, are exceptionally effective as single agent therapies in NSCLC with adenocarcinoma histology that carry L858R and/or exon 19 deletion EGFR mutations (Lynch T J et al., N Engl J Med 350: 2129 (2004), Paez J G. et al. Science 304: 1497 (2004)). Patients with these sensitizing EGFR mutations have shown ~70% response rate with these EGFR kinase inhibitors which exceeds the response rate for conventional chemotherapy. However, despite the substantial initial response, these cancers eventually develop resistance against the kinase inhibitors. In general, the resistance mechanisms against EGFR therapies can be divided into three major categories: (1) EGFR mutations such as EGFRvIII and T790M mutations, (2) mutations that lead to activation of EGFR downstream pathways such as mutation of PIK3CA, RAS and PTEN, and (3) activation of compensatory pathways such as MET and IGF1R pathways. The discovery of various mechanisms of resistance against EGFR targeted therapies presents a new challenge for subsequent generation of EGFR therapies.

The two EGFR antagonistic antibodies, cetuximab and panitumumab inhibit the EGFR signaling through blockade of ligand binding (Gill et al., J Biol Chem, 259:7755-7760 (1984), Goldstein et al., Clin Cancer Res, 1:1311-1318 (1995), Prewett et al., Clin Cancer Res, 4:2957-2966 (1998)). Cetuximab treatment improves overall and progression-free survival, and preserves the quality of life in patients with colorectal cancer that has not responded to chemotherapy. However, cetuximab treatment has no clinical benefit for colorectal cancer patients with KRAS mutations which are frequently found in codon 12 and 13 (Karapetis C et al., N Engl J Med 359: 1757 (2008)). Similarly, in SCCHN, EGFR antibodies are less effective in cancers that carry the exon 2-7 deletion mutation of EGFR (EGFRvIII) (Sok J. et al. Clin Cancer Res 12: 5064 (2006)). Thus, there is a need for new cancer treatments that can overcome common mechanisms of resistance to EGFR-targeted therapies.

BRIEF SUMMARY OF THE INVENTION

The invention relates to the identification that EGFR antibody immunoconjugates are effective in inhibiting the growth of tumor cells that are resistant to anti-EGFR therapies. In a particular embodiment, the EGFR antibody immunoconjugates are effective in inhibiting the growth of tumor cells that are also anaplastic lymphoma kinase (ALK) inhibitor resistant.

Thus, in one embodiment, the invention provides a method of inhibiting the growth of EGFR-expressing tumor cells that are resistant or refractory to EGFR therapy comprising contacting said tumor cells with an effective amount of an EGFR antibody immunoconjugate. In one embodiment, the EGFR therapy to which the cells are resistant is selected from the group consisting of: erlotinib, gefitinib, lapatinib, BIB2992, cetuximab, panitumumab, zalutumumab, necitumumab, and nimotuzumab. In another embodiment, at least one of the tumor cells: (1) contains one or more mutations in an EGFR encoding gene; (2) contains one or more mutations in a PIK3CA, RAS, or PTEN encoding gene; (3) has an activated MET or IGF1R pathway; (4) has mesenchymal histology or undergoes epithelial-mesenchymal transition; or (5) has ERBB2 gene amplification or increased production of HER2 protein. In another embodiment, the EGFR mutations comprise an EGFRvIII or T790M mutation. In another embodiment, at least one tumor cell has an activated EGFR downstream pathway, for example by mutation of PIK3CA, RAS or PTEN encoding genes. In another embodiment, at least one tumor cell has an activated alternative pathway(s) such as: the MET or IGF1R pathway. In one embodiment, MET activation is caused by MET gene amplification and/or MET ligand expression.

In certain embodiments, the EGFR antibody immunoconjugates are effective in inhibiting the growth of EGFR-resistant/refractory tumor cells that are also anaplastic lymphoma kinase (ALK) inhibitor resistant. In one embodiment, at least one of the tumor cells contain a EML4-ALK translocation. In another embodiment, the tumor cells are non-small cell lung tumors.

The invention also provides a method of treating cancer in a patient comprising administering an effective amount of an EGFR antibody immunoconjugate to inhibit growth of the tumor cells in said patient, wherein at least one of the tumor cells: (1) contains one or more mutations in an EGFR encoding gene; (2) contains one or more mutations in a PIK3CA, RAS, or PTEN encoding gene; (3) has an activated MET or IGF1R pathway; (4) has mesenchymal histology or undergoes epithelial-mesenchymal transition; or (5) has ERBB2 gene amplification or increased production of HER2 protein. In one embodiment, MET activation is caused by MET gene amplification.

The invention also provides a method of treating cancer in a patient comprising (a) identifying tumor cells from said patient that (1) contain one or more mutations in an EGFR encoding gene; (2) contain one or more mutations in a PIK3CA, RAS, or PTEN encoding gene; (3) has an activated MET or IGF1R pathway; (4) have mesenchymal histology or undergo epithelial-mesenchymal transition; or (5) have ERBB2 gene amplification or increased production of HER2 protein; and (b) administering an effective amount of an EGFR antibody immunoconjugate to said patient. In one embodiment, MET activation is caused by MET gene amplification. In one embodiment, the cancer is squamous cell carcinoma, lung cancer, head and neck cancer, or EGFR-positive cancers.

In one embodiment, the patients previously failed or are currently failing an EGFR therapy. In another embodiment, the therapy comprised administration of an EGFR antibody or an EGFR kinase inhibitor. In another embodiment, the EGFR antibody is cetuximab or panitumumab. In another embodiment, the EGFR kinase inhibitor is erlotinib or gefitinib.

In certain embodiments, the EGFR antibody immunoconjugates are effective in treating cancer in a patient that contains one or more ALK inhibitor resistant tumor cells. In one embodiment, at least one of the tumor cells contain a EML4-ALK translocation. In another embodiment, the tumor cells are non-small cell lung tumors.

In one embodiment, the antibody immunoconjugate has the formula (A)-(L)-(C), wherein: (A) is an antibody or antigen binding fragment thereof that specifically binds EGFR; (L) is a linker; and (C) is a cytotoxic agent; and wherein said linker (L) links (A) to (C). In another embodiment, the EGFR antibody comprises the heavy chain variable region of SEQ ID NO: 1 and the light chain variable region of SEQ ID NOs: 2 or 3. In another embodiment, the linker is selected from the group consisting of a cleavable linker, a non-cleavable linker, a hydrophilic linker, and a dicarboxylic acid based linker. In another embodiment, the linker is a non-cleavable linker. In another embodiment, the linker is selected from the group consisting: N-succinimidyl 4-(2-pyridyldithio)pentanoate (SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl)cyclohexanecarboxylate (SMCC); N-sulfosuccinimidyl 4-(maleimidomethyl)cyclohexanecarboxylate (sulfoSMCC); N-succinimidyl-4-(iodoacetyl)-aminobenzoate (SIAB); N-succinimidyl-[(N-maleimidopropionamido)-tetraethyleneglycol]ester (NHS-PEG4-maleimide), N-(beta-maleimidopropyloxy)succinimide ester (BMPS); and gamma-maleimidobutyric acid N-succinimidyl ester (GMBS). In another embodiment, the cytotoxic agent is selected from the group consisting of a maytansinoid, maytansinoid analog, doxorubicin, a modified doxorubicin, benzodiazepine, taxoid, CC-1065, CC-1065 analog, duocarmycin, duocarmycin analog, calicheamicin, dolastatin, dolastatin analog, aristatin, tomaymycin derivative, and leptomycin derivative or a prodrug of the agent. In another embodiment, the cytotoxic agent is a maytansinoid. In another embodiment, the cytotoxic agent is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4). In another embodiment, the EGFR antibody immunoconjugate comprises an antibody which comprises the heavy chain variable region of SEQ ID NO: 1 and the light chain variable region of SEQ ID NOs: 2 or 3; the linker SMCC; and the maytansinoid DM1.

In one embodiment, the antibody immunoconjugate is administered with at least one additional anti-neoplastic agent. In another embodiment, the EGFR antibody immunoconjugate is administered simultaneously with the anti-neoplastic agent. In another embodiment, the EGFR antibody immunoconjugate and anti-neoplastic agent are administered in any temporal order. In another embodiment, the patient is a human.

In certain embodiments, the treatment involves the combined administration of an EGFR immunoconjugate of the present invention and at least one additional targeted therapy. Useful classes of targeted therapies include, but not limited to, for example, (1) HER2 inhibitors, (2) EGFR inhibitors (e.g., tyrosine kinase inhibitors or targeted anti-EGFR antibodies), (3) BRAF inhibitors, (4) ALK inhibitors, (5) hormone receptor inhibitors, (6) mTOR inhibitors, (7) VEGF inhibitors, or (8) cancer vaccines. A tyrosine kinase inhibitor can be specific for EGFR or can be multi-specific and can inhibit the activity or one or more kinases other than or in addition to EGFR.

BRIEF DESCRIPTION OF THE DRAWINGS/FIGURES

FIG. 1 is a line graph depicting the cytotoxic activity of the huEGFR-7R naked antibody and the huEGFR-7R-SMCC-DM1 conjugate against NCI-H1975 NSCLC tumor cell line that carries L858R and T790M EGFR mutations.

FIG. 2 is a line graph depicting the cytotoxic activity of erlotinib against HCC827 NSCLC cell line in presence or absence of 50 ng/mL hepatocyte growth factor (HGF).

FIG. 3 are line graphs depicting the cytotoxic activity of cetuximab, the huEGFR-7R naked antibody and the huEGFR-7R-SMCC-DM1 conjugate against HCC827 NSCLC cell line in absence (A) or presence (B) of 50 ng/mL HGF.

FIG. 4 is a line graph depicting the cytotoxic activity of the huEGFR-7R naked antibody and the huEGFR-7R-SMCC-DM1 conjugate against NCI-H226, a mesenchymal NSCLC cell line.

FIG. 5 depicts the characterization of erlotinib-resistant HCC827 NSCLC cell line. (A) is a line graph depicting the cytotoxic activity of erlotinib against the parental HCC827 cell line and the erlotinib-resistant HCC827-ER cell line. (B) are histologic pictures of the parental HCC827 cell line and the erlotinib-resistant HCC827-ER cell line. (C) is a Western blot analysis of the parental HCC827 cell line and the erlotinib-resistant HCC827-ER cell line.

FIG. 6 shows flow cytometry histograms depicting the expression of EGFR, HER3 and MET on the parental HCC827 cell line and the erlotinib-resistant HCC827-ER cell line.

FIG. 7 is a line graph depicting the cytotoxic activity of erlotinib against the parental HCC827 cell line, the erlotinib-resistant HCC827-ER and HCC827-ER-E4 cell lines.

FIG. 8 shows Western blot analysis of the parental HCC827 cell line and the erlotinib-resistant HCC827-ER-E4 cell line after 16 hour treatment of erlotinib at the indicated dose.

FIG. 9 are line graphs depicting the cytotoxic activity of cetuximab, the huEGFR-7R naked antibody and the huEGFR-7R-SMCC-DM1 conjugate against the parental HCC827 cell line and the erlotinib-resistant HCC827-ER-E4 cell line.

FIG. 10 is a line graph depicting the cytotoxic activity of the huEGFR-7R-SMCC-DM1 conjugate against the SW620 colorectal adenocarcinoma cell line that carries G12V KRAS mutation.

FIG. 11 is a line graph depicting the cytotoxic activity of cetuximab, the huEGFR-7R naked antibody and the huEGFR-7R-SMCC-DM1 conjugate against the Detroit562 squamous cell carcinoma of head and neck (SCCHN) cell line that carries H1047R PIK3CA mutation.

FIG. 12 shows the cytotoxic activity of huEGFR-7R antibody, huEGFR-7R-SMCC-DM1 conjugate, chKTI-SMCC-DM1 conjugate, cetuximab, and erlotinib against the parental HCC827 cells (A), erlotinib-resistant HCC827 ER cells (B) and HCC827 EPR cells (C).

FIG. 13 shows the cytotoxic activities of crizotinib and erlotinib (A); and of huEGFR-7R antibody, huEGFR-7R-SMCC-DM1 conjugate, chKTI-SMCC-DM1 conjugate, and cetuximab (B) against H2228 NSCLC adenocarcinoma cell line that carries EML4-ALK gene translocation.

DETAILED DESCRIPTION OF THE INVENTION

The present invention relates to the discovery that EGFR antibody conjugates are useful in treating tumor cells that are resistant to EGFR therapies, including unconjugated EGFR antibodies and/or ALK inhibitors. In particular, antibody drug conjugates that comprise EGFR antibodies having the capacity to inhibit tumor cell growth driven by the EGFR pathway while having limited effect on normal cells expressing EGFR such as skin keratinocytes were shown to be effective against EGFR-therapy resistant tumors. Importantly, the EGFR antibody component alone, similar to other EGFR inhibitors, is ineffective against tumor cells resistant to EGFR targeted therapies. However, when coupled to a maytansinoid payload, the conjugate surprisingly exhibits robust activity against tumor cells with diverse resistance mechanisms to EGFR inhibitors.

I. DEFINITIONS

To facilitate an understanding of the present invention, a number of terms and phrases are defined below.

"Epidermal growth factor receptor" or "EGFR" is a tyrosine kinase cell surface receptor. The term "soluble EGFR" or "sEGFR" refers to a portion of EGFR containing the extracellular, ligand-binding domain of EGFR. More specifically, sEGFR contains amino acids 1-619 of mature EGFR (Ullrich et al., Human Epidermal Growth Factor cDNA Sequence and Aberrant Expression of the Amplified Gene in A-431 Epidermoid Carcinoma Cells, Nature, Vol. 309, 418-25 (1986)). As used herein, "epidermal growth factor receptor" or "EGFR" is meant to encompass not only wild-type or full-length EGFR, but also all mutant forms of EGFR, some forms of which are described herein below.

By "EGFRvIII" is meant a variant of EGFR in which exons 2 through 7 are deleted resulting in a 267 amino acid in-frame deletion in the extracellular domain of EGFR. EGFRvIII is also known as type III mutant, delta-EGFR, EGFRde2-7, and ΔEGFR and is described in U.S. Pat. Nos. 6,455,498, 6,127,126, 5,981,725, 5,814,317, 5,710,010, 5,401,828, and 5,212,290.

By "a deleted EGFR variant" is meant a deletion variant of EGFR in which a portion of the extracellular domain is missing, such that EGFR signaling becomes at least partially ligand-independent.

By "ALK inhibitor" is meant anti-cancer drugs that act on tumors with variations of anaplastic lymphoma kinase (ALK), such as an EML4-ALK translocation. EML4-ALK translocations result in EML4-ALK positive cancers. EML4-ALK positive cancer refers to a primary malignant tumor whose cells contain a characteristic abnormal configuration of DNA wherein the echinoderm microtubule-associated protein-like 4 (EML4) gene is fused to the ALK gene. This abnormal gene fusion leads to the production of a protein (EML4-ALK) that appears, in many cases, to promote and maintain the malignant behavior of the cancer cells.

The term "K-ras mutant" refers to a K-ras protein comprising at least one amino acid mutation as compared to wild-type K-ras (or to a nucleotide sequence encoding such a K-ras protein). K-ras mutants may include, but are not limited to, allelic variants, splice variants, substitution variants, deletion variants, and insertion variants. The term "K-ras mutation" refers to at least one amino acid mutation in the sequence of a K-ras protein as compared to the wild-type sequence (or to a nucleotide sequence encoding such a K-ras protein). The terms "K-ras mutant tumor" or "tumor comprising (or comprises) a K-ras mutation" are used interchangeably herein and refer to a population of tumor cells wherein a K-ras mutation can be detected, at either the protein or nucleotide level. The term "cancer comprising (or comprises) a K-ras mutation" as used herein refer to a population of cancer cells wherein a K-ras mutation can be detected, at either the protein or nucleotide level. K-ras, as well as EGFR mutations, can be detected by techniques and methods known to one of skill in the art including, but not limited to, PCR-based assays (e.g., polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays), direct sequencing, primer extension reactions, electrophoresis, oligonucleotide ligation assays, hybridization assays, TaqMan assays, SNP genotyping assays, high resolution melting assays and microarray analyses.

The term "activating mutation" refers to a mutation that results in constitutive activation of a protein, for example, K-ras, and constitutive activation of a signaling pathway. In some embodiments, a K-ras protein comprising an activating mutation initiates constitutive activity of several pathways including, but not limited to, the MAP kinase cascade and the PI3 kinase cascade. In some embodiments, constitutive activity by the K-ras mutant and signaling pathways contributes significantly to several aspects of the malignant phenotype, including deregulation of cellular proliferation, impaired differentiation, reduced apoptosis and prolonged cell survival.

The phrase "EGFR mediated cancer" refers to a cancer characterized by epithelial tumors in which EGFR is abnormally activated to levels greater than in normal, corresponding epithelial tissue. These greater levels of EGFR activity promote tumor growth in many types of cancer. Such cancers include, but are not limited to, non-small cell lung cancer, breast cancer, colorectal cancer, head and neck cancers, prostate cancer and glioblastoma multiforme. Abnormal activation of EGFR can arise from overexpression of the receptor, gene amplification, activating mutations, overexpression of receptor ligands, and/or loss of regulators of EGFR activity.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as EGFR. In some embodiments, blocking antibodies or antagonist antibodies substantially or completely inhibit the biological activity of the antigen. The biological activity can be reduced by 10%, 20%, 30%, 50%, 70%, 80%, 90%, 95%, or even 100%.

The phrase "ability to inhibit EGFR activation" with respect to an antibody as used herein, is intended to refer to an antibody whose binding to EGFR results in inhibition of human EGFR activation and the biological activity of human EGFR that occurs upon activation of the receptor. Measuring one or more indicators of EGFR biological activity as determined using either a cell proliferation assay, an apoptosis assay, a receptor binding assay, a receptor phosphorylation assay, or a mouse tumor model can assess an antibody's ability to inhibit EGFR activation.

The term "anti-EGFR antibody" or "an antibody that binds to EGFR" refers to an antibody that is capable of binding EGFR with sufficient affinity such that the antibody is useful as a diagnostic and/or therapeutic agent in targeting EGFR. Several anti-EGFR antibodies are known in the art. For example, cetuximab (Ab 225) and 528 Ab are described in U.S. Pat. No. 4,943,533, which is herein incorporated by reference.

The extent of binding of an anti-EGFR antibody to an unrelated, non-EGFR protein can be less than about 10% of the binding of the antibody to EGFR as measured, e.g., by a radioimmunoassay (RIA). In certain embodiments, an antibody that binds to EGFR has a dissociation constant (Kd) of ≤1 µM, ≤100 nM, ≤10 nM, ≤1 nM, or ≤0.1 nM. In other embodiments, the antibody binds to EGFR with a dissociation constant between about 100 nM and about 0.1 nM, between about 10 nM and about 0.1 nM, or between about 1 nM and about 0.1 nM.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, Nature, 321:522-525; Riechmann et al., 1988, Nature, 332:323-327; Verhoeyen et al., 1988. Science, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)).

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody. The difference between two "substantially similar binding affinities" is generally less than about 10% as a function of the value for the reference/comparator antibody.

"Ligand-independent binding" as used herein denotes the ability of the EGFR binding agents to bind an epitope on human EGFR in the absence of ligand interaction with EGFR.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-EGFR antibody or fragment thereof) and is defined by a generic formula: C-L-A, wherein C=cytotoxin, L=linker, and A=cell binding agent or anti-EGFR antibody or antibody fragment. Immunoconjugates can also be defined by the generic formula in reverse order: A-L-C.

A "linker" is any chemical moiety that is capable of linking a compound, usually a drug, such as a maytansinoid, to a cell-binding agent such as an anti-EGFR antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. "Tumor" and "neoplasm" refer to one or more cells that result from excessive cell growth or proliferation, either benign (noncancerous) or malignant (cancerous) including pre-cancerous lesions. Examples of "cancer" or "tumorigenic" diseases which can be treated and/or prevented include neoplasms of the abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent or stop) cancer cell infiltration into peripheral organs; inhibit (i.e., slow to some extent or stop) tumor metastasis; inhibit, to some extent, tumor growth; and/or relieve to some extent one or more of the symptoms associated with the cancer. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The word "label" when used herein refers to a detectable compound or composition which is conjugated directly or indirectly to the antibody so as to generate a "labeled" antibody. The label can be detectable by itself (e.g. radioisotope labels or fluorescent labels) or, in the case of an enzymatic label, can catalyze chemical alteration of a substrate compound or composition which is detectable.

A "chemotherapeutic agent" is a chemical compound useful in the treatment of cancer, regardless of mechanism of action.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; or some combination of effects.

The phrase "substantially non-responsive" as used herein refers to a tumor or a cancer that shows stable growth or increased growth after administration of a therapeutic agent. The phrase may refer to a patient that shows stable disease or progressive disease after administration of a therapeutic agent. The phrase may be used when referring to tumors or cancers that are resistant to treatment with a therapeutic agent. The phrase "substantially non-responsive to an EGFR inhibitor" as used herein refers to a tumor or a cancer that shows stable growth or increased growth after administration of an EGFR inhibitor. In some embodiments, an EGFR inhibitor is administered to a patient in need of treatment, and "substantially non-responsive" to the EGFR inhibitor includes: no reduction in the number of, or continued growth of, cancer cells; no reduction in the tumor size; an increase in tumor size; no inhibition of, or a continuation of, cancer cell infiltration into peripheral organs including, for example, the spread of cancer into soft tissue and bone; no inhibition of, or a continuation of, tumor metastasis; no inhibition of, or a continuation of, tumor growth; no or little relief of one or more symptoms associated with the specific cancer; no or little reduction in tumorigenicity, tumorgenic frequency, or tumorgenic capacity of a tumor; no or little reduction in the number or frequency of cancer stem cells in a tumor; or some combination of effects.

As used herein, an illness that is "refractory" to therapy is one that is initially unresponsive, becomes unresponsive over time (e.g., within three months (i.e., disease progression may be observed on or within three months of treatment)) or recurs shortly after discontinuation of treatment. In some embodiments, a cancer that is "refractory" to therapy is one in which that cancer does not respond to treatment.

As used herein, an illness that is "resistant" to therapy is one that is unresponsive to therapy. In one embodiment, the cancer may be resistant at the beginning of treatment or it may become resistant during, treatment. In certain embodiments, a "refractory" cancer is also termed a "resistant" cancer.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. EGFR ANTIBODIES

Antibodies or antigen binding fragments thereof that specifically bind EGFR (i.e., "EGFR antibodies") can be used to generate EGFR immunoconjugates that are useful in the present invention. The present invention includes the use of any type of EGFR antibody or EGFR-binding fragments, portions, or other antigen binding forms thereof. These include, for example, but without limitation various forms of antibodies and fragments thereof such as polyclonal or monoclonal antibodies or antigen-binding fragments thereof; chimeric, primatized, humanized, fully human antibodies or antigen-binding fragments thereof; or epitope binding fragments of antibodies such as single-chain, Fv, sFv, scFv, Fab, Fab', and F(ab')2 (Parham, J. Immunol. 131:2895-2902 (1983); Spring et al, J. Immunol. 113:470-478 (1974); Nisonoff et al, Arch. Biochem. Biophys. 89:230-244 (1960)).

Particularly useful EGFR antibodies for generation of EGFR immunoconjugates are described in co-pending US Appl. Pub. No. 2012/0156217. One such antibody, huEGFR-7R is a humanized antibody that comprises the heavy chain variable region of SEQ ID NO: 1 and the light chain variable region of SEQ ID NOs: 2 or 3.

analogs, duocarmycins and duocarmycin analogs, enediynes, such as calicheamicins, dolastatin and dolastatin analogs including auristatins, tomaymycin derivatives, leptomycin derivatives, methotrexate, cisplatin, carboplatin, daunorubicin, doxorubicin, vincristine, vinblastine, melphalan, mitomycin C, chlorambucil and morpholino doxorubicin.

Immunoconjugates can be prepared by using a linking group in order to link a drug or prodrug to the antibody or functional equivalent. Suitable linking groups are well known in the art and include, for example, disulfide groups, thioether groups, acid labile groups, photolabile groups, peptidase labile groups and esterase labile groups.

The drug or prodrug can, for example, be linked to the anti-EGFR antibody or fragment thereof through a disulfide bond. The linker molecule or crosslinking agent comprises a reactive chemical group that can react with the anti-EGFR antibody or fragment thereof. The reactive chemical groups for reaction with the cell-binding agent can be N-succinimidyl esters and N-sulfosuccinimidyl esters. Additionally the linker molecule comprises a reactive chemical group, which can be a dithiopyridyl group that can react with the drug to form a disulfide bond. Linker molecules include, for example, N-succinimidyl 3-(2-pyridyldithio)propionate (SPDP) (see, e.g., Carlsson et al., Biochem. J., 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)-2-sulfobutanoate (sulfo-SPDB) (see US Publication No. 2009/0274713), N-succinimidyl 4-(2-pyridyldithio) pentanoate (SPP) (see, e.g., CAS Registry number 341498-08-6), 2-iminothiolane, or acetylsuccinic anhydride. For example, the antibody or cell binding agent can be modified with crosslinking reagents and the antibody or cell binding

```
huEGFR-7R    QVQLVQSGAEVAKPGASVKLSCKASGYTFTSYWMQWVKQRPGQGLECIGTIYP
V_H          GDGDTTYTQKFQGKATLTADKSSSTAYMQLSSLRSEDSAVYYCARYDAPGYAM
             DYWGQGTLVTVSS
             (SEQ ID NO: 1)

huEGFR-7R    DIQMTQSPSSLSASVGDRVTITCRASQDINNYLAWYQHKPGKGPKLLIHYTSTLH
VL v1.0      P
             GIPSRFSGSGSGRDYSFSISSLEPEDIATYYCLQYDNLLYTFGQGTKLEIKR
             (SEQ ID NO: 2)

huEGFR-7R    DIQMTQSPSSLSASVGDRVTITCKASQDINNYLAWYQHKPGKGPKLLIHYTSTLH
VL v1.01     P
             GIPSRFSGSGSGRDYSFSISSLEPEDIATYYCLQYDNLLYTFGQGTKLEIKR
             (SEQ ID NO: 3)
```

Other EGFR antibodies are known in the art. These antibodies include necitumumab, cetixumab, panitumumab, nimotuzumab, zalutumumab, mAb 806 (J Clin Invest. 2007; 117(2):346-352).

III. EGFR IMMUNOCONJUGATES

The present invention is also directed to conjugates (also referred to herein as immunoconjugates), comprising the anti-EGFR antibodies, antibody fragments, and their functional equivalents as disclosed herein, linked or conjugated to a drug or prodrug. Suitable drugs or prodrugs are known in the art. The drugs or prodrugs can be cytotoxic agents. The cytotoxic agent used in the cytotoxic conjugate of the present invention can be any compound that results in the death of a cell, or induces cell death, or in some manner decreases cell viability, and includes, for example, maytansinoids and maytansinoid analogs. Other suitable cytotoxic agents are for example benzodiazepines, taxoids, CC-1065 and CC-1065 agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration.

In another aspect of the present invention, the anti-EGFR antibody is linked to cytotoxic drugs via disulfide bonds and a polyethylene glycol spacer in enhancing the potency, solubility or the efficacy of the immunoconjugate. Such cleavable hydrophilic linkers are described in WO2009/134976 and WO2003/068144. The additional benefit of this linker design is the desired high monomer ratio and the minimal aggregation of the antibody-drug conjugate. Specifically contemplated in this aspect are conjugates of cell-binding agents and drugs linked via disulfide group (—S—S—) bearing polyethylene glycol spacers (($CH_2CH_2O)_{n=1-14}$) with a narrow range of drug load of 2-8. These conjugates show relatively high potent biological activity toward cancer cells and have the desired biochemical properties of high conjugation yield and high monomer ratio with minimal protein aggregation.

Specifically contemplated in this aspect is an anti-EGFR antibody drug conjugate of formula (I) or a conjugate of formula (I'):

$$CB—[X_l—(—CH_2—CH_2O—)_n—Y-D]_m \qquad (I)$$

$$[D-Y—(—CH_2—CH_2O—)_n—X_l]_m—CB \qquad (I')$$

wherein:
CB represents an anti-EGFR antibody or fragment;
D represents a drug;
X represents an aliphatic, an aromatic or a heterocyclic unit attached to the cell-binding agent via a thioether bond, an amide bond, a carbamate bond, or an ether bond;
Y represents an aliphatic, an aromatic or a heterocyclic unit attached to the drug via a disulfide bond;
l is 0 or 1;
m is an integer from 2 to 8; and
n is an integer from 1 to 24. In some embodiments, m is an integer from 2 to 6. In some embodiments, m is an integer from 3 to 5. In some embodiments, n is an integer form 2 to 8.

Alternatively, as disclosed in, for example, U.S. Pat. Nos. 6,441,163 and 7,368,565, the drug can be first modified to introduce a reactive ester suitable to react with a cell-binding agent. Reaction of these drugs containing an activated linker moiety with a cell-binding agent provides another method of producing a cell-binding agent drug conjugate. Maytansinoids can also be linked to anti-EGFR antibody or fragment using PEG linking groups, as set forth for example in U.S. Pat. No. 6,716,821. These PEG non-cleavable linking groups are soluble both in water and in non-aqueous solvents, and can be used to join one or more cytotoxic agents to a cell binding agent. Exemplary PEG linking groups include heterobifunctional PEG linkers that react with cytotoxic agents and cell binding agents at opposite ends of the linkers through a functional sulfhydryl or disulfide group at one end, and an active ester at the other end. As a general example of the synthesis of a cytotoxic conjugate using a PEG linking group, reference is again made to U.S. Pat. No. 6,716,821 which is incorporated entirely by reference herein. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, to yield a cytotoxic conjugate comprising one or more cytotoxic agents covalently bonded to a cell binding agent through a PEG linking group. Alternatively, the cell binding can be modified with the bifunctional PEG crosslinker to introduce a reactive disulfide moiety (such as a pyridyldisulfide), which can then be treated with a thiol-containing maytansinoid to provide a conjugate. In another method, the cell binding can be modified with the bifunctional PEG crosslinker to introduce a thiol moiety which can then can be treated with a reactive disulfide-containing maytansinoid (such as a pyridyldisulfide), to provide a conjugate.

Antibody-maytansinoid conjugates with non-cleavable linkers can also be prepared. Such crosslinkers are described in the art (see US Publication No. 2005/0169933) and include but are not limited to, N-succinimidyl 4-(N-maleimidomethyl)cyclohexane-1-carboxylate (SMCC), N-(beta-maleimidopropyloxy)succinimide ester (BMPS); and gamma-maleimidobutyric acid N-succinimidyl ester (GMBS). In some embodiments, the antibody is modified with crosslinking reagents such as succinimidyl 4-(N-maleimidomethyl)-cyclohexane-1-carboxylate (SMCC), sulfo-SMCC, m-maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)). The modified antibody is then reacted with the thiol-containing maytansinoid derivative to produce a conjugate. The conjugate can be purified by gel filtration through a Sephadex G25 column or by dialysis or tangential flow filtration. The modified antibodies are treated with the thiol-containing maytansinoid (1 to 2 molar equivalent/maleimido group) and antibody-maytansinoid conjugates are purified by gel filtration through a Sephadex G-25 column, chromatography on a ceramic hydroxyapatite column, dialysis or tangential flow filtration or a combination of methods thereof. Typically, an average of 1-10 maytansinoids per antibody are linked. One method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result. Maytansinoid conjugates of antibodies, antibody fragments, and other proteins are made in the same way.

In another aspect of the invention, the EGFR antibody is linked to the drug via a non-cleavable bond through the intermediacy of a PEG spacer. Suitable crosslinking reagents comprising hydrophilic PEG chains that form linkers between a drug and the anti-EGFR antibody or fragment are also well known in the art, or are commercially available (for example from Quanta Biodesign, Powell, Ohio). Suitable PEG-containing crosslinkers can also be synthesized from commercially available PEGs themselves using standard synthetic chemistry techniques known to one skilled in the art. The drags can be reacted with bifunctional PEG-containing cross linkers to give compounds of the following formula, $Z—X_l—(—CH_2—CH_2—O—)_n—Y_p-D$, by methods described in detail in US Patent Publication 2009/0274713 and in WO2009/134976, which can then react with the cell binding agent to provide a conjugate. Alternatively, the cell binding agent can be modified with the bifunctional PEG crosslinker to introduce a thiol-reactive group (such as a maleimide or haloacetamide) which can then be treated with a thiol-containing maytansinoid to provide a conjugate. In another method, the cell binding agent can be modified with the bifunctional PEG crosslinker to introduce a thiol moiety which can then be treated with a thiol-reactive maytansinoid (such as a maytansinoid bearing a maleimide or haloacetamide), to provide a conjugate.

Accordingly, another aspect of the present invention is an anti-EGFR antibody drug conjugate of formula (II) or of formula (II'):

$$CB—[X_l—(—CH_2—CH_2—O—)_n—Y_p-D]_m \qquad (II)$$

$$[D-Y_p—(—CH_2—CH_2—O—)_n—X_l]_m—CB \qquad (II')$$

wherein, CB represents an anti-EGFR antibody or fragment;
D represents a drag;
X represents an aliphatic, an aromatic or a heterocyclic unit bonded to the cell-binding agent via a thioether bond, an amide bond, a carbamate bond, or an ether bond;
Y represents an aliphatic, an aromatic, or a heterocyclic unit bonded to the drug via a covalent bond selected from the group consisting of a thioether bond, an amide bond, a carbamate bond, an ether bond, an amine bond, a carbon-carbon bond and a hydrazone bond;

l is 0 or 1;

p is 0 or 1;

m is an integer from 2 to 15; and n is an integer from 1 to 2000.

In some embodiments, m is an integer from 2 to 8; and

In some embodiments, n is an integer from 1 to 24.

In some embodiments, m is an integer from 2 to 6.

In some embodiments, m is an integer from 3 to 5.

In some embodiments, n is an integer from 2 to 8. Examples of suitable PEG-containing linkers include linkers having an N-succinimidyl ester or N-sulfosuccinimidyl ester moiety for reaction with the anti-EGFR antibody or fragment thereof, as well as a maleimido- or haloacetyl-based moiety for reaction with the compound. A PEG spacer can be incorporated into any crosslinker known in the art by the methods described herein.

Many of the linkers disclosed herein are described in detail in U.S. Patent Publication Nos. 2005/0169933 and 2009/0274713, and in WO2009/134976; the contents of which are entirely incorporated herein by reference.

The present invention includes aspects wherein about 2 to about 8 drug molecules ("drug load"), for example, maytansinoid, are linked to an anti-EGFR antibody or fragment thereof, the anti-tumor effect of the conjugate is much more efficacious as compared to a drug load of a lesser or higher number of drugs linked to the same cell binding agent. "Drug load", as used herein, refers to the number of drug molecules (e.g., a maytansinoid) that can be attached to a cell binding agent (e.g., an anti-EGFR antibody or fragment thereof). In one aspect the number of drug molecules that can be attached to a cell binding agent can average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). $N^{2'}$-deacetyl-$N^{2'}$-(3-mercapto-1-oxopropyl)-maytansine (DM1) and $N^{2'}$-deacetyl-$N^{2'}$-(4-mercapto-4-methyl-1-oxopentyl)maytansine (DM4) can be used.

The anti-EGFR antibody or fragment thereof can be modified by reacting a bifunctional crosslinking reagent with the anti-EGFR antibody or fragment thereof, thereby resulting in the covalent attachment of a linker molecule to the anti-EGFR antibody or fragment thereof. As used herein, a "bifunctional crosslinking reagent" is any chemical moiety that covalently links a cell-binding agent to a drug, such as the drugs described herein. In another method, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

The drug molecules can also be linked to the antibody molecules through an intermediary carrier molecule such as serum albumin.

As used herein, the expression "linked to a cell-binding agent" or "linked to an anti-EGFR antibody or fragment" refers to the conjugate molecule comprising at least one drag derivative bound to a cell-binding agent anti-EGFR antibody or fragment via a suitable linking group, or a precursor thereof. One linking group is SMCC.

In certain embodiments, cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

In a certain embodiment, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (III):

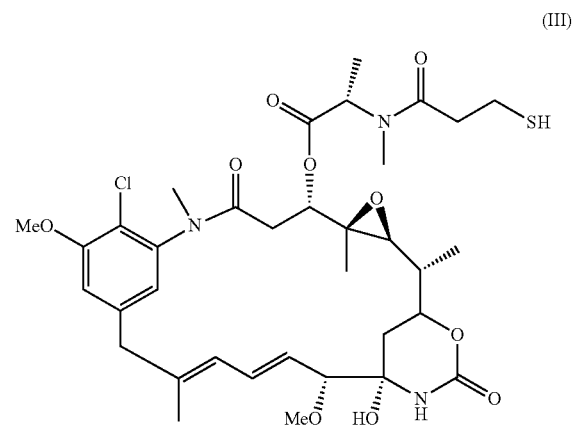 [SMILES: COc1cc2cc(c1Cl)N(C)C(=O)C[C@H](OC(=O)[C@H](C)N(C)C(=O)CCS)[C@]1(C)O[C@H]1[C@H](C)C1C[C@@](O)(NC(=O)O1)[C@H](OC)/C=C/C=C(\C)C2]

(III)

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula (IV):

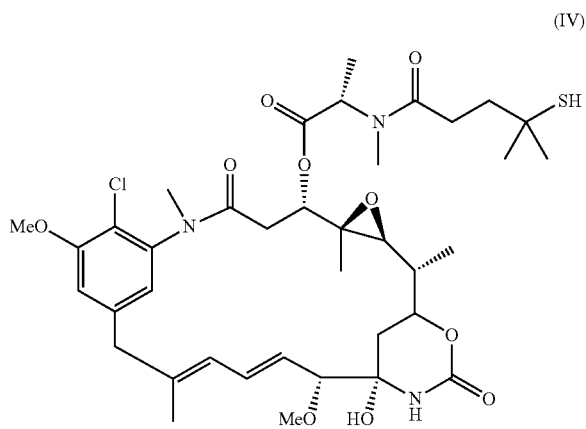 [SMILES: COc1cc2cc(c1Cl)N(C)C(=O)C[C@H](OC(=O)[C@H](C)N(C)C(=O)CCC(C)(C)S)[C@]1(C)O[C@H]1[C@H](C)C1C[C@@](O)(NC(=O)O1)[C@H](OC)/C=C/C=C(\C)C2]

(IV)

Another maytansinoid comprising a side chain that contains a sterically hindered thiol bond is $N^{2'}$-deacetyl-N-$^{2'}$(4-mercapto-1-oxopentyl)-maytansine (termed DM3), represented by the following structural formula (V):

(V)

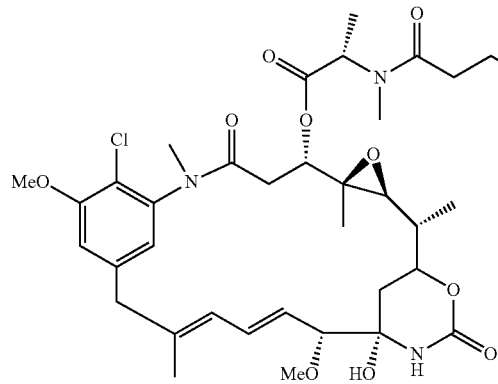

Each of the maytansinoids taught in U.S. Pat. Nos. 5,208, 020 and 7,276,497, can also be used in the conjugate of the present invention. In this regard, the entire disclosure of U.S. Pat. Nos. 5,208,020 and 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety.

Structural representations of some conjugates are shown below:

(VI)

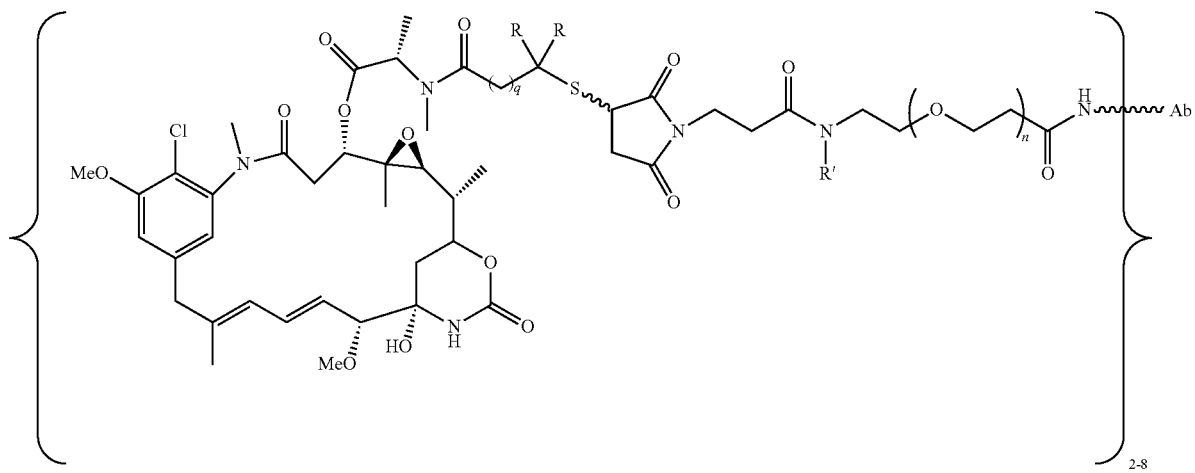

Ab = Antibody
R' = H or Me
DM1: R = H, q =1
DM4: R = CH$_3$, q = 2
n = 1 - 24
Ab-PEG-Mal-DM1/DM4

(VII)

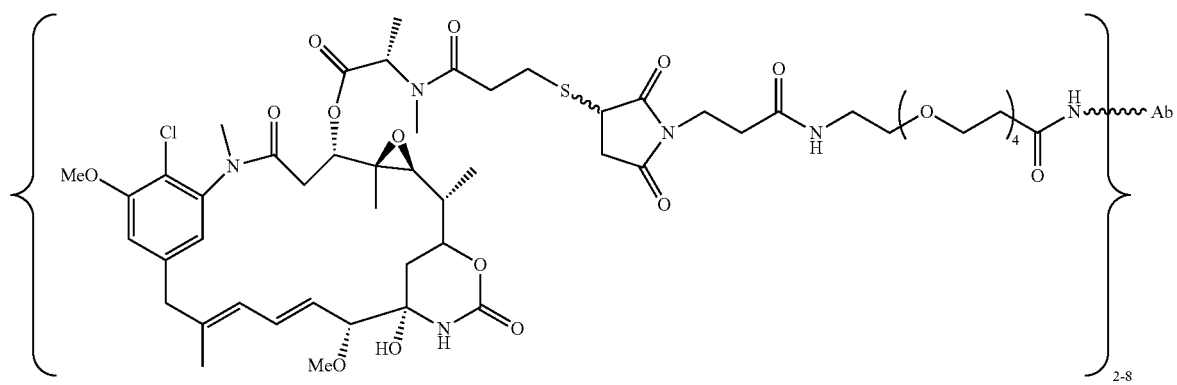

Ab = Antibody
Ab-PEG4-Mal-DM1

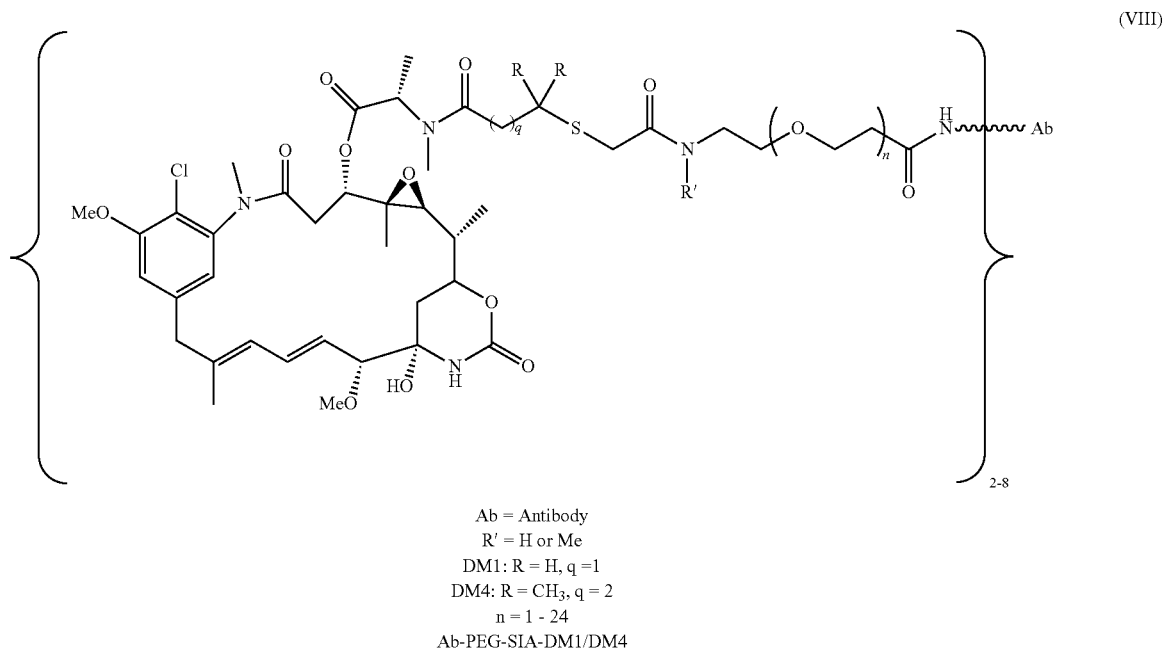
Ab = Antibody
R' = H or Me
DM1: R = H, q = 1
DM4: R = CH₃, q = 2
n = 1 - 24
Ab-PEG-SIA-DM1/DM4
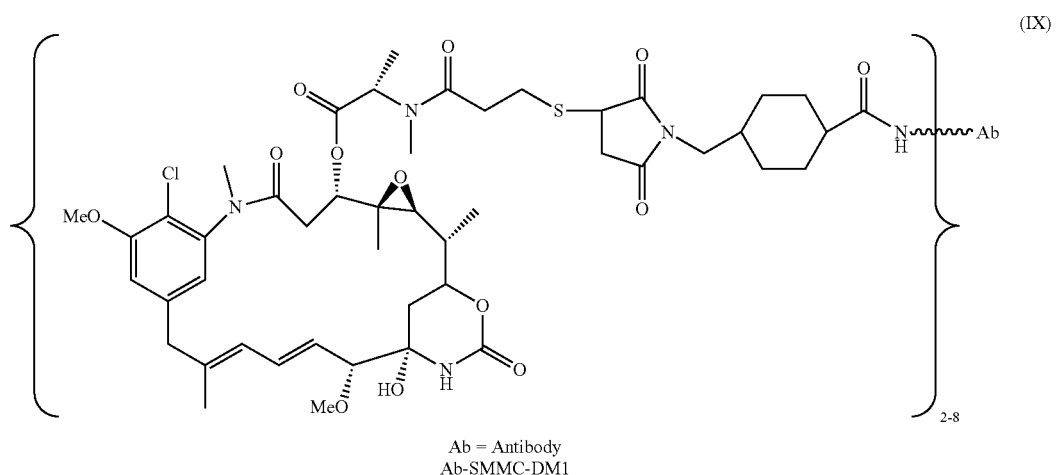
Ab = Antibody
Ab-SMMC-DM1
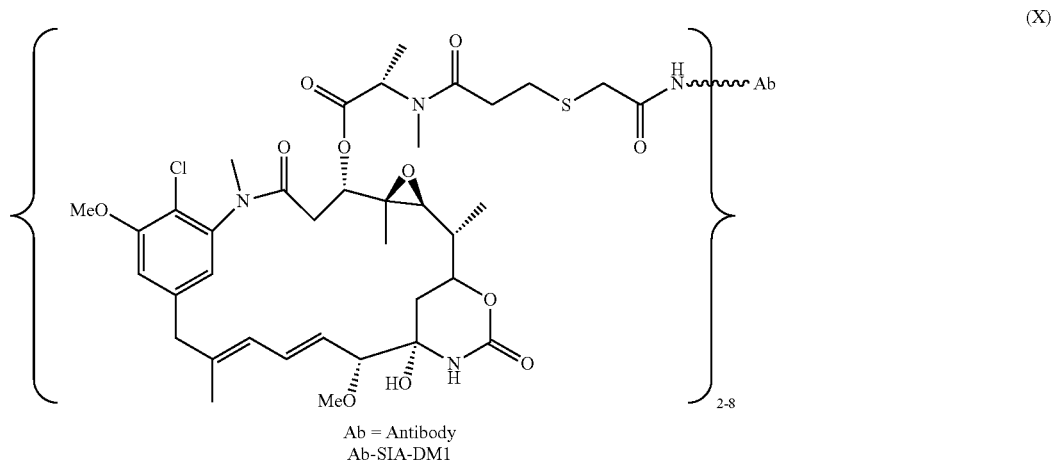
Ab = Antibody
Ab-SIA-DM1

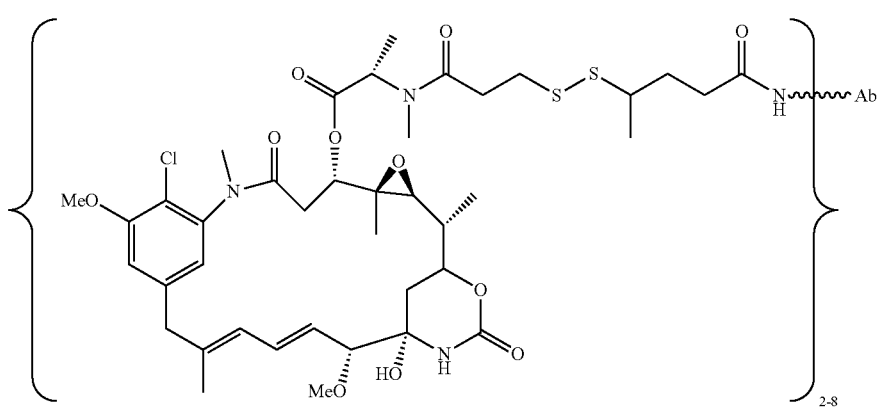

Ab = Antibody
Ab-SPP-DM1

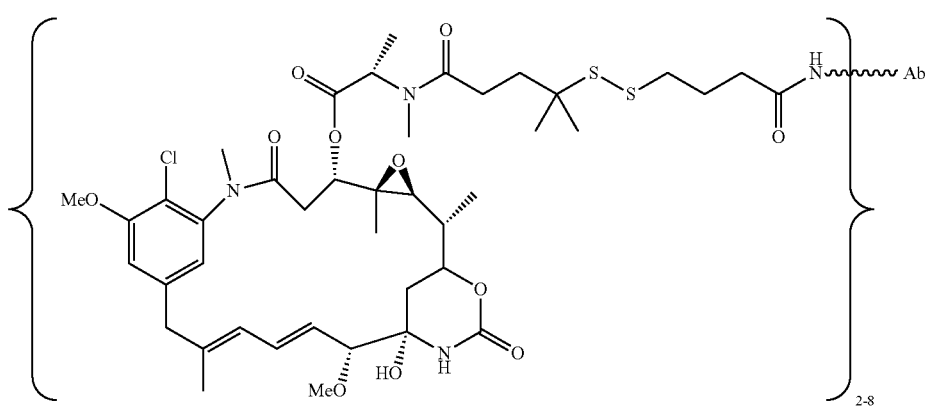

Ab = Antibody
Ab-SPDB-DM4

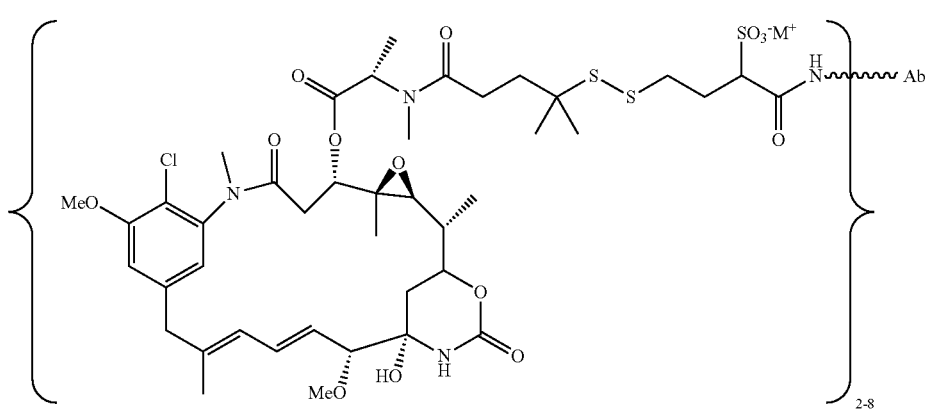

Ab = Antibody
M⁺ = H⁺ or a
cation (e.g., Na⁺)
Ab-sulfo-SPDB-DM4

The invention also includes various isomers and mixtures of maytansinoids and conjugates described herein (for example, maytansinoids of formulae (III)-(V) and conjugates of formulae (VI)-(XIII)), Certain compounds and conjugates of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms.

When a chiral center is not defined as R or S, either a pure enantiomer or a mixture of both configurations is present "Racemate" or "racemic mixture" means a compound of equimolar quantities of two enantiomers, wherein such mixtures exhibit no optical activity; i.e., they do not rotate the plane of polarized light.

Several descriptions for producing such antibody-maytansinoid conjugates are provided in U.S. Pat. Nos. 6,333,410, 6,441,163, 6,716,821, and 7,368,565, each of which is incorporated herein in its entirety.

In general, a solution of an antibody in aqueous buffer can be incubated with a molar excess of maytansinoids having a disulfide moiety that bears a reactive group. The reaction mixture can be quenched by addition of excess amine (such as ethanolamine, taurine, etc.). The maytansinoid-antibody conjugate can then be purified by gel filtration.

The number of maytansinoid molecules bound per antibody molecule can be determined by measuring spectrophotometrically the ratio of the absorbance at 252 nm and 280 nm. The average number of maytansinoid molecules/antibody can be, for example, 1-10 or 2-5.

Anthracycline compounds, as well as derivatives, intermediates and modified versions thereof, can also be used to prepare anti-EGFR immunoconjugates. For example, doxorabicin, doxorubicin derivatives, doxorubicin intermediates, and modified doxorubicins can be used in anti-EGFR conjugates. Exemplary compounds are described in WO 2010/009124, which is herein incorporated by reference in its entirety. Such compounds include, for example, compounds of the following formula:

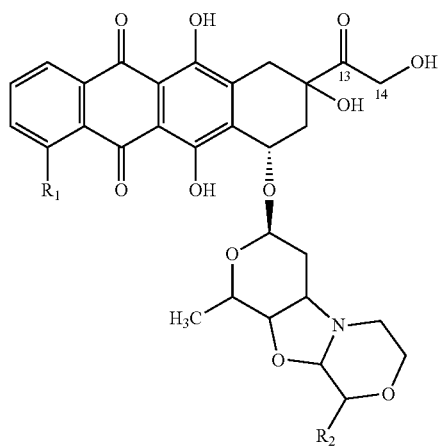

wherein $R_1$ is a hydrogen atom, hydroxy or methoxy group and $R_2$ is a $C_1$-$C_8$ alkoxy group, or a pharmaceutically acceptable salt thereof.

Conjugates of antibodies with maytansinoid or other drugs can be evaluated for their ability to suppress proliferation of various unwanted cell lines in vitro. For example, cell lines such NCI-H226, NCI-H292, and NCI-H322M, can easily be used for the assessment of cytotoxicity of these compounds. Cells to be evaluated can be exposed to the compounds for 4 to 5 days and the surviving fractions of cells measured in direct assays by known methods. $IC_{50}$ values can then be calculated from the results of the assays.

The immunoconjugates can, according to some embodiments described herein, be internalized into cells. The immunoconjugate, therefore, can exert a therapeutic effect when it is taken up by, or internalized, by a EGFR-expressing cell. In some particular embodiments, the immunoconjugate comprises an antibody, antibody fragment, or polypeptide, linked to a cytotoxic agent by a cleavable linker, and the cytotoxic agent is cleaved from the antibody, antibody fragment, or polypeptide, wherein it is internalized by a EGFR-expressing cell.

In some embodiments, the immunoconjugates are capable of reducing tumor volume. For example, in some embodiments, treatment with an immunoconjugate results in a % T/C value that is less than about 50%, less than about 45%, less than about 40%, less than about 35%, less than about 30%, less than about 25%, less than about 20%, less than about 15%, less than about 10%, or less than about 5%.

In another aspect of the invention siRNA molecules can be linked to the antibodies of the present invention instead of a drug. siRNAs can be linked to the antibodies of the present invention by methods commonly used for the modification of oligonucleotides (see, for example, US Patent Publications 20050107325 and 20070213292). Thus the siRNA in its 3' or 5'-phosphoromidite form can be reacted with one end of the crosslinker bearing a hydroxyl functionality to give an ester bond between the siRNA and the crosslinker. Similarly reaction of the siRNA phosphoramidite with a crosslinker bearing a terminal amino group results in linkage of the crosslinker to the siRNA through an amine. Alternatively, the siRNA can be derivatized by standard chemical methods to introduce a thiol group. This thiol-containing siRNA can be reacted with an antibody that has been modified to introduce an active disulfide or maleimide moiety, to produce a cleavable or non-cleavable conjugate. Between 1-20 siRNA molecules can be linked to an antibody by this method.

IV. METHODS OF TREATMENT

As described above, the EGFR immunoconjugates of the invention are useful in inhibiting the growth of tumor cells that are substantially non-responsive to EGFR therapies and/or ALK inhibitors. In certain embodiments, the immunoconjugates are useful for inhibiting tumor growth, reducing tumor volume, and/or reducing the tumorigenicity of a tumor. The methods of use can be in vitro, ex vivo, or in vivo methods.

In certain embodiments, the disease treated with the EGFR immunoconjugate is a cancer that carries intrinsic resistance or acquires resistance to EGFR targeting unconjugated antibodies and/or small molecule ALK inhibitors. In one embodiment, the disease is characterized as containing one or more tumor cells which intrinsically comprise characteristics (e.g. somatic mutations) which make the cells resistant to EGFR therapies. In certain embodiments, the cancer is characterized by one or more EGFR expressing cells in which (1) the cells contain one or more mutations in an EGFR encoding gene, (2) the cells contain one or more mutations in a PIK3CA, RAS or PTEN encoding gene, (3) the cells contain compensatory pathways such as MET and IGF pathways that are activated, or (4) other molecular changes such as epithelial-mesenchymal transition are present. Epithelial-mesenchymal transition or transformation is a biological process that allows a polarized epithelial cell to undergo multiple biochemical changes that enable it to assume a mesenchymal cell phenotype, which includes enhanced migratory capacity, invasiveness, elevated resistance to apoptosis, and greatly increased production of extracellular membrane components.

In certain embodiments, the cancer is characterized by EGFR expressing cells in which there is (1) EGFR gene amplification, (2) mutation of PIK3CA, for example, H1047R, (3) RAS mutation, for example in KRAS codon 12 and 13, (4) PTEN downregulation or loss, (5) MET activation via MET gene amplification, MET overexpression and/or HGF overexpression, (6) IGF1R activation, (7) activation of AKT, or (8) activation of ERK1/2.

In certain embodiments, the disease treated with the EGFR immunoconjugates is a cancer in which the tumor cells have acquired resistance to EGFR therapies. In such embodiments, the tumor cells have acquired resistance to drugs which are used as the standard of care, such that these drugs are no longer effective in treating the tumor cells. In one embodiment, the EGFR standard of care therapies include, but are not limited to, EGFR kinase inhibitors such as erlotinib, gefitinib, lapatinib, and BIB2992, and anti-EGFR antibodies such as cetuximab, panitumumab, zalutumumab, necitumumab, and nimotuzumab.

In certain embodiments, the disease treated with EGFR immunoconjugates is a cancer in which the tumor cells are resistant to ALK inhibitor therapy. In such embodiments, the tumor cells have acquired resistance to drugs which are used as the standard of care, such that these drugs are no longer effective in treating the tumor cells. In one embodiment, the ALK inhibitor standard of care therapy includes, but is not limited to, crizotinib.

In certain embodiments, the tumor cells are initially susceptible to standard EGFR therapies and acquire resistance to the therapies over time. In certain embodiments, the tumor cells acquire resistance through somatic mutations. In one embodiment, disease progression while on treatment or within 6 months of treatment with an EGFR standard of care drug is indicative that the EGFR standard of care drug is no longer effective. In another embodiment, disease progression while on treatment or within 12 months of treatment with an EGFR standard of care drug is indicative that the EGFR standard of care drug is no longer effective. In certain embodiments, one of ordinary skill in the art may determine disease progression by testing a tumor sample for the presence of molecular markers indicative of tumor cells that have acquired resistance to EGFR standard of care therapies. In certain embodiments, one of ordinary skill in the art may determine disease progression by standard imaging measures, tumor biomarker assessment or signs of clinical deterioration.

In a further aspect, the invention is directed to an improved method for treating cell proliferation disorders wherein EGFR is abnormally expressed, including cancers of the bladder, brain, head and neck, pancreas, lung, breast, ovary, colon, prostate, skin, and kidney, comprising administering a therapeutically effective amount of an anti-EGFR binding agent of the present invention to a human subject in need thereof. In another embodiment the antibody is humanized. Examples of cell proliferation disorders that can be treated by an anti-EGFR binding agent of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system.

Similarly, other cell proliferation disorders can also be treated by the EGFR immunoconjugates of the present invention. Examples of such cell proliferation disorders include, but are not limited to: adrenal cortex hyperplasia (Cushing's disease), congenital adrenal hyperplasia, endometrial hyperplasia, benign prostatic hyperplasia, breast hyperplasia, intimal hyperplasia, focal epithelial hyperplasia (Heck's disease), sebaceous hyperplasia, compensatory liver hyperplasia, and any other cell proliferation disease, besides neoplasia, located in an organ system listed above.

In some embodiments, the method of inhibiting tumor growth comprises contacting the tumor or tumor cells with the EGFR immunoconjugates in vivo. In certain embodiments, contacting a tumor or tumor cell with an EGFR immunoconjugates is undertaken in an animal model. For example, EGFR immunoconjugates can be administered to xenografts expressing one or more mutated EGFRs that have been grown in immunocompromised mice (e.g. NOD/SCID mice) to inhibit tumor growth. In some embodiments, cancer stem cells are isolated from a patient sample such as, for example, a tissue biopsy, pleural effusion, or blood sample and injected into immunocompromised mice that are then administered a EGFR immunoconjugate to inhibit tumor cell growth. In some embodiments, the EGFR immunoconjugate is administered at the same time or shortly after introduction of tumorigenic cells into the animal to prevent tumor growth. In some embodiments, the EGFR immunoconjugate is administered as a therapeutic after the tumorigenic cells have grown to a specified size.

In certain embodiments, the method of inhibiting EGFR-therapy-resistant tumor growth comprises administering to a subject a therapeutically effective amount of a EGFR immunoconjugate. In certain embodiments, the subject is a human. In certain embodiments, the subject has a tumor or has had a tumor removed.

In addition, the invention provides a method of reducing the tumorigenicity of a tumor in a subject, comprising administering a therapeutically effective amount of a EGFR immunoconjugate to the subject. In certain embodiments, the tumor comprises cancer stem cells. In certain embodiments, the frequency of cancer stem cells in the tumor is reduced by administration of the immunoconjugate.

The pharmaceutical compositions comprising the EGFR immunoconjugates of the invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

In certain embodiments, in addition to administering the EGFR immunoconjugate, the method or treatment further comprises administering a second anti-cancer agent (prior to, concurrently with, and/or subsequently to administration of the EGFR immunoconjugate).

It will be appreciated that the combination of a EGFR immunoconjugate and a second anti-cancer agent may be administered in any order or concurrently. In selected embodiments, the EGFR immunoconjugate will be administered to patients that have previously undergone treatment with the second anti-cancer agent. In certain other embodiments, the EGFR immunoconjugate and the second anti-cancer agent will be administered substantially simultaneously or concurrently. For example, a subject may be given the EGFR immunoconjugate while undergoing a course of treatment with the second anti-cancer agent (e.g., chemotherapy). In certain embodiments, the EGFR immunoconjugate will be administered within 1 year of the treatment with the second anti-cancer agent. In certain alternative embodiments, the EGFR immunoconjugate will be administered within 10, 8, 6, 4, or 2 months of any treatment with the second anti-cancer agent. In certain other embodiments, the EGFR immunoconjugate will be administered within 4, 3, 2, or 1 week of any treatment with the second anti-cancer agent. In some embodiments, the EGFR immunoconjugate will be administered within 5, 4, 3, 2, or 1 days of any treatment with the second anti-cancer agent. It will further be appreciated that the two agents or treatment may be administered to the subject within a matter of hours or minutes (i.e., substantially simultaneously).

Useful classes of anti-cancer agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics antifolates, antimetabolites, chemotherapy sensitizers, duocarmycins, etoposides, fluorinated pyrimidines, ionophores, lexitropsins, nitrosoureas, platinols, performing compounds, purine antimetabolites, puromycins, radiation sensitizers, steroids, taxanes, topoisomerase inhibitors, vinca alkaloids, or the like. In certain embodiments, the second anti-cancer agent is an antimetabolite, an antimitotic, a topoisomerase inhibitor, or an angiogenesis inhibitor.

Anticancer agents that may be administered in combination with the EGFR immunoconjugates include chemotherapeutic agents. Thus, in some embodiments, the method or treatment involves the combined administration of an immunoconjugate of the present invention and a chemotherapeutic agent or cocktail of multiple different chemotherapeutic agents. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

In certain embodiments, the treatment involves the combined administration of an EGFR immunoconjugate of the present invention and radiation therapy. Treatment with the EGFR immunoconjugate can occur prior to, concurrently with, or subsequent to administration of radiation therapy. Any dosing schedules for such radiation therapy can be used as determined by the skilled practitioner.

In certain embodiments, the treatment involves the combined administration of an EGFR immunoconjugate of the present invention and other targeted therapy. Useful classes of targeted therapies include, but not limited to, for example, (1) HER2 inhibitors, (2) EGFR inhibitors (e.g., tyrosine kinase inhibitors or targeted anti-EGFR antibodies), (3) BRAF inhibitors, (4) ALK inhibitors, (5) hormone receptor inhibitors, (6) mTOR inhibitors, (7) VEGF inhibitors, or (8) cancer vaccines. A tyrosine kinase inhibitor can be specific for EGFR or can be multi-specific and can inhibit the activity or one or more kinases other than or in addition to EGFR. Treatment with the EGFR immunoconjugate can occur prior to, concurrently with, or subsequent to administration of targeted therapy.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Example 1

The huEGFR-7R-SMCC-DM1 Conjugate is Effective Against NSCLC Cell Line with T7901 EGFR Mutation EGFR mutation T790M is one of the most common mechanism of resistance against EGFR tyrosine kinase inhibitors, erlotinib and gefitinib (Suda K. et al. Clin Cancer Res 16: 5489 (2010); Sequist L. et al. Sci Transl Med 3: 75ra26 (2011); and Uramoto H. et al. Lung Cancer 73: 361 (2011)). To test the capacity of the huEGFR-7R-SMCC-DM1 conjugate to overcome T790M mediated resistance, an in vitro cytotoxic assay was performed using NCI-H1975 cell line. NCI-H1975 cell line is a NSCLC adenocarcinoma cell line that carries both sensitizing (L858R) and resistant (T790M) EGFR mutations (Cosmic database, Wellcome Trust Sanger Institute), thus it closely mimics the EGFR kinase inhibitor resistant tumors found in the clinical setting.

The cytotoxic assay was performed as follows. Target cells were plated at 1,500 to 3,000 cells per well in 100 μL complete RPMI media containing 10% fetal bovine serum (FBS). Test articles were diluted into complete RPMI media using 5-fold dilution series and 100 μL were added per well. The final concentration typically ranged from $3 \times 10^{-8}$ M to $8 \times 10^{-14}$ M. Cells were incubated at 37° C. in a humidified 5% $CO_2$ incubator for 4-5 days. Viability of the remaining cells was determined by colorimetric WST-8 assay and the absorbance at 450 nm (A450) was measured in a multi-well plate reader. The surviving fraction was calculated by dividing each treated sample value by the average value of untreated controls. The surviving fraction value was plotted against the test article concentration in a semi-log plot for each treatment.

As shown in FIG. 1, the huEGFR-7R-SMCC-DM1 conjugate was effective in killing the NCI-H1975 cells with EC50 of 3 nM. In contrast, the huEGFR-7R naked antibody did not have any effect and the non-binding control conjugate, chKTI-SMCC-DM1, only killed the tumor cells with EC50 of 10 nM or 3 fold higher concentration than the huEGFR-7R-SMCC-DM1 conjugate. These data suggest that the huEGFR-7R-SMCC-DM1 conjugate can overcome T790M-mediated EGFR kinase inhibitor resistance mechanism.

Example 2

The huEGFR-7R-SMCC-DM1 Conjugate can Overcome MET/HGF Mediated EGFR Kinase Inhibitor Resistant Mechanism Activation of MET signaling through MET gene amplification, MET protein overexpression and/or overexpression of HGF, a MET ligand, is the second most common mechanism of resistance against EGFR kinase inhibitors, gefitinib or erlotinib (Uramoto H. et al. Lung Cancer 73: 361 (2011)). Yano et al. (Cancer Res 68: 9479 (2008)) has shown that HGF, but not EGFR ligands (EGF and TGF-α) or IGF1R ligand (IGF-1), can induce gefitinib resistance in lung adenocarcinoma cell lines with EGFR-sensitizing mutations. The experiment shown in FIG. 2 confirmed this finding. In this experiment, the HCC827 cell line that carries exon 19 deletion EGFR sensitizing mutation (Yano et al. Cancer Res 68: 9479 (2008)) was incubated with the increasing dose of erlotinib in presence or absence of 50 ng/mL hepatocyte growth factor (HGF). In absence of HGF, erlotinib can effectively inhibit the tumor cell growth (EC50=0.9 nM). However, addition of 50 ng/mL HGF makes the HCC827 cells strongly resistant to erlotinib-mediated cell inhibition.

This in vitro system was then used to test the cytotoxic activity of the huEGFR-7R-SMCC-DM1 conjugate. As shown in FIG. 3, the huEGFR-7R-SMCC-DM1 conjugate was very effective in inhibiting HCC827 cells in absence (FIG. 3A) or presence (FIG. 3B) of HGF (Table 1). Cetuximab and the huEGFR-7R naked antibodies showed marginal activities against HCC827 cells and this activity was further reduced in the presence of HGF. These data suggest that the huEGFR-7R-SMCC-DM1 conjugate can overcome EGFR kinase inhibitor resistance mediated by activation of MET/HGF pathway.

TABLE 1

| EC50 of the huEGFR-7R-SMCC-DM1 conjugate | | |
|---|---|---|
| | HCC827 | HCC827 + HGF |
| huEGFR-7R-SMCC-DM1 | 0.065 nM | 0.069 nM |

Example 3

The huEGFR-7R-SMCC-DM1 Conjugate is Effective Against Tumor Cell Line with Mesenchymal Histology NSCLC cell lines with mesenchymal histology are generally more resistant to gefitinib than those with epithelial histology (Yauch R L. et al. Clin Cancer Res 11: 8686 (2005)). To test the cytotoxic activity of the huEGFR-7R-SMCC-DM1 conjugate against gefitinib-resistant mesenchymal lung cancer line, a cytotoxic assay with 11226 cell line was performed as described in Example 1. H226 cell line is a squamous cell carcinoma with mesenchymal histology. Despite of high EGFR expression, H226 cell line is resistant to gefitinib (Yauch R L. et al. Clin Cancer Res 11: 8686 (2005)). As shown in FIG. 4, the huEGFR-7R-SMCC-DM1 conjugate was very effective against H226 cell line with EC50=0.14 nM. In contrast, neither the huEGFR-7R antibody nor cetuximab had effect on H226 tumor cell growth. The non-binding control conjugate, chKTI-SMCC-DM1 was only cytotoxic at ~160 fold higher concentration than the huEGFR-7R-SMCC-DM1 conjugate. These data suggest that the huEGFR-7R-SMCC-DM1 conjugate is highly effective in lung cancer cell line with mesenchymal histology that is resistant to EGFR kinase inhibitors and cetuximab.

Example 4

Generation and Characterization of Erlotinib-Resistant NSCLC Adenocarcinoma Cell Line To further evaluate the cytotoxic activity of the huEGFR-7R-SMCC-DM1 conjugate in EGFR kinase inhibitor resistant setting, erlotinib-resistant HCC827 cell line was generated. HCC827 cell line carries exon 19 deletion EGFR mutation that makes it very sensitive to the EGFR kinase inhibitors including erlotinib (Yano et al. Cancer Res 68: 9479 (2008)) (FIGS. 2 and 5A). In brief, HCC827 cell line was cultured continuously for more than 4 months in presence of increasing concentration of erlotinib starting at 2 nM until 2 uM. The resulting HCC827-ER cell line was highly resistant to erlotinib compared to the parental cell line (FIG. 5A). Intriguingly, the histology of the HCC827 cells changed from epithelial to mesenchymal when they acquired resistance to erlotinib (FIG. 5B). This histological change was accompanied by changes in molecular markers. The parental cell line was E-cadherin (an epithelial marker) positive and vimentin (a mesenchymal marker) negative while the erlotinib-resistant HCC827-ER cell line was E-cadherin negative and vimentin positive (FIG. 5C). As shown in FIG. 6, the HCC827-ER cell line still expressed EGFR but at significantly lower level compared to the parental line. The cell surface expression of HER3 and MET were also decreased in the erlotinib-resistant HCC827-ER cell line. The antibody binding per cell (ABC) shown in FIG. 6 represents antigen density on the cell surface; it was measured using PE-Quantibrite beads (BD bioscience) and the indicated antibodies against the corresponding antigens that are labeled with PE at 1:1 ratio.

HCC827-ER cell line was further subcloned by limiting dilution. As shown in FIG. 7, the resulting subclone HCC827-ER-E4 cell line maintained erlotinib resistance as the HCC827-ER cell line and the EGFR antigen density was further decreased to 53,000. To characterize this cell line in more detail, HCC827-ER-E4 cells were cultured in absence of erlotinib for one week and treated with different dose of erlotinib for 16 hours. The cell lysates were collected, separated by SDS-PAGE and analyzed by Western blot. As shown in FIG. 8, the HCC827-ER-E4 cell line maintained the mesenchymal marker (E-cadherin negative and vimentin positive). In parallel with the FACS data (FIG. 6), the EGFR level was significantly reduced compared to the parental HCC827 cell line. The EGFR phosphorylation in both cell lines was completely inhibited in presence of erlotinib. In contrast to the HCC827 parental cell line, HER3 phosphorylation was completely absent in the HCC827-ER-E4 cell line. There was no change in PTEN level. Interestingly, the AKT level in HCC827 parental line was reduced by erlotinib treatment in dose dependent manner, while it was not changed in HCC827-ER-E4 cell line. In parallel, in the HCC827 cell line, the AKT phosphorylation was inhibited by erlotinib, while in the HCC827-ER-E4 cell line, there was little change in the phospho AKT (pAKT) level. Similar to the pAKT, erlotinib inhibited ERK1/2 phosphorylation in the HCC827 parental line but it had less impact on the HCC827-ER-E4 cell line. Furthermore, DNA sequencing of EGFR exons 19, 20 and 21 did not reveal any additional mutations besides the exon 19 deletion. Altogether, these data demonstrate that in the presence of erlotinib, the HCC827-ER-E4 cell line can maintain AKT and ERK1/2 signaling pathways, the two important signaling pathways downstream of the EGFR pathway. The absence of EGFR and HER3 activations in the HCC827-ER-E4 cell line suggests that this cell line has developed a compensatory pathway mechanism that triggers the AKT and ERK1/2 signaling pathways but that is not affected by erlotinib.

The huEGFR-7R-SMCC-DM1 Conjugate is Effective Against Erlotinib-Resistant HCC827-ER-E4 Cell Line To test the activity of the huEGFR-7R-SMCC-DM1 conjugate, an in vitro cytotoxicity assay as described in Example 1 was performed with HCC827-ER and HCC827-ER-E4 cell lines. As shown in FIG. 9 and Table 2, huEGFR-7R-SMCC-DM1 was very effective in killing the erlotinib-resistant cells despite of significant reduction in antigen density. The EC50 value of the huEGFR-7R-SMCC-DM1 conjugate on the erlotinib-resistant cell lines were comparable to that on the parental HCC827 cell line (Table 1). Cetuximab, the huEGFR-7R antibody and the non-binding control conjugate, chKTI-SMCC-DM1 had little effect on the erlotinib-resistant cell lines.

TABLE 2

EC50 of the huEGFR-7R-SMCC-DM1 conjugate

|  | HCC827-ER | HCC827-ER-E4 |
|---|---|---|
| huEGFR-7R-SMCC-DM1 | 0.031 nM | 0.035 nM |

Example 5

The huEGFR-7R-SMCC-DM1 Conjugate is Effective Against Cetuximab-Resistant Colorectal and Head and Neck Cancer Cell Lines Cetuximab (Erbitux) is approved for treatment of colorectal and head and neck cancers. Treatment with cetuximab improves overall and progression-free survival and preserves the quality of life in patients with colorectal cancer that has not responded to chemotherapy. However, cetuximab treatment has no benefit for patients that carry KRAS mutations which are frequently found in codon 12 and 13 (Karapetis C et al., N Engl J Med 359: 1757 (2008)). To test if the huEGFR-7R-SMCC-DM1 conjugate can overcome cetuximab resistance mediated by KRAS mutation, an in vitro cytotoxicity assay using SW620, a colorectal cancer cell line that carries G12V KRAS mutation (Cosmic database, Wellcome Trust Sanger Institute), was performed as described in Example 1. As shown in FIG. 10, the huEGFR-7R-SMCC-DM1 conjugate was effective in killing the SW620 tumor cells with EC50 of 4.1 nM. The non-binding conjugate control, chKTI-SMCC-DM1, can also kill the tumor cells but it requires ten-fold higher concentration (EC50=~39 nM).

PIK3CA mutations are associated with trastuzumab (Herceptin) resistance in HER2+ metastatic breast cancer (Kataoka Y. et al., Ann Oncol 21: 255 (2010); Lee J Y. et al., Science 317: 206 (2007)) and cetuximab (Erbitux) resistance in head and neck cancer (Rebucci M. et al., Int J Oncol 38: 189 (2011)). To investigate if the huEGFR-7R-SMCC-DM1 conjugate can overcome the resistance mediated by PIK3CA mutation, an in vitro cytotoxicity assay using Detroit 562, a SCCHN cancer cell line that carries one of the most common H1047R PIK3CA mutation (Cosmic database, Wellcome Trust Sanger Institute), was performed as described in Example 1. As shown in FIG. 11, the huEGFR-7R-SMCC-DM1 conjugate was very effective in inhibiting Detroit562 tumor cell growth with EC50 of 0.62 nM. The non-binding conjugate control, chKTI-SMCC-DM1, also killed the tumor cells but the EC50 was 19 nM, 30 fold higher than that of the huEGFR-7R-SMCC-DM1 conjugate. In contrast, cetuximab and the huEGFR-7R antibody had no effect on the tumor cell growth. Altogether, these data strongly suggest that the huEGFR-7R-SMCC-DM1 conjugate can overcome various resistance mechanisms against cetuximab.

Example 6

The huEGFR-7R-SMCC-DM1 Conjugate is Effective Against Erlotinib-Resistant HCC827 NSCLC Cell Line with T790M EGFR Mutation and MET Gene Amplification To further demonstrate the activity of IMGN289 against NSCLC cells that are resistant to EGFR inhibitors, an in vitro cytotoxicity assay was performed with HCC827 ER (Aichi) and HCC827 EPR (Aichi) cell lines which were generated in the laboratory of Dr. Mitsudomi (Department of Thoracic Surgery, Aichi Cancer Center Hospital, Nagoya, Japan) by growing erlotinib-sensitive HCC827 cells (parental HCC827 cells) in increasing concentration of erlotinib or erlotinib and PHA665,752 (MET inhibitor), respectively (Suda K. et al. Clin Cancer Res 16: 5489 (2010)). As shown in Suda K. et al. Clin Cancer Res 16: 5489 (2010) and FIG. 12, the HCC827 ER and HCC827 EPR cells are significantly more resistant to erlotinib than the parental HCC827 cells. The EC50s of erlotinib in parental HCC827, HCC827 ER (Aichi) and HCC827 EPR cells were 2.94E-10 M, ~7.28E-6 M, and ~5.84E-6M, respectively (Table 3). The HCC827 ER cell line contains high MET gene copy number and the HCC827 EPR cell line carries T790M EGFR mutation (Suda K. et al. Clin Cancer Res 16: 5489 (2010)). These cell lines reflect the two major mechanisms of resistance against EGFR tyrosine kinase inhibitors (Sequist L. et al. Sci Transl Med 3: 75ra26 (2011)). The EGFR antigen density on the parental HCC827, HCC827 ER and HCC827 EPR cell lines are 192,600, 32,500 and 421,600, respectively.

The cytotoxicity assay result (FIG. 12) shows that the parental HCC827 (Aichi) cells are highly sensitive to EGFR signaling inhibition by erlotinib, cetuximab and huEGFR-7R antibody with EC50s in 1E-10M range (Table 3). In contrast, HCC827 ER and EPR (Aichi) cells are highly resistant to erlotinib, cetuximab and huEGFR-7R antibody. Importantly, the huEGFR-7R-SMCC-DM1 conjugate is very effective against the erlotinib-resistant cell lines with MET gene amplification and T790M EGFR mutation. Altogether, these data strongly suggest that the huEGFR-7R-SMCC-DM1 conjugate can overcome various resistance mechanisms against the EGFR tyrosine kinase inhibitors.

TABLE 3

EC50s anti-EGFR agents against parental HCC827, HCC827 ER and HCC827 EPR cells

|  | Parental HCC827 (Aichi) | HCC827 ER (Aichi) | HCC827 EPR (Aichi) |
|---|---|---|---|
| huEGFR-7R | 4.26E-10M | NA | NA |
| huEGFR-7R-SMCC-DM1 | 1.29E-10M | 3.09E-11M | 5.96E-11M |
| chKTI-SMCC-DM1 | ~1.91E-8M | ~9.18E-9M | ~2.37E-8M |
| Cetuximab | 1.46E-10M | NA | NA |
| Erlotinib | 2.94E-10M | ~7.28E-6M | ~5.84E-6M |

Example 7

The huEGFR-7R-SMCC-DM1 conjugate is effective against crizotinib-resistant EML4-ALK+ H2228 NSCLC Cell Line EML4-ALK gene translocation leads to a constitutive activation of ALK kinase and has been identified as a driver mutation in ~5% of NSCLC adenocarcinoma (reviewed in Castro-Carpeno J. et al., Clin Transl Oncol. 13:774-779 (2011)). Crizotinib, an ALK inhibitor, is very effective against tumors with EML4-ALK gene translocation and was recently approved by the FDA for the treatment of ALK positive NSCLC. Unfortunately, ~40% of EML4-ALK+ tumors are resistant to crizotinib. Additionally, tumors that are sensitive to crizotinib can rapidly develop resistance to the drug (Castro-Carpeno J. et al., Clin Transl Oncol. 13:774-779 (2011)). H2228 is an NSCLC adenocarcinoma cell line with the EML4-ALK gene translocation that is resistant to the ALK tyrosine kinase inhibitor, TAE684 (Koivunen J P. et al., Clin Cancer Res 14:4275-4283 (2008)). In our experiments, H2228 cells were also resistant to crizotinib (EC50=3.82E-6 M) (FIG. 13A). Since H2228 cells expressed a relatively high level of EGFR (116,000 antigen/cell), we tested the activity of erlotinib, cetuximab, huEGFR-7R antibody and huEGFR-7R-SMCC-DM1 conjugate in this cell line. As shown in FIGS. 13A and 13B, erlotinib was only active at a high dose (EC50=2.61E-5 M). The erlotinib activity in this cell line is comparable to that in EGFR inhibitor-resistant HCC827 cell line (see example 6), suggesting that H2228 cells are inherently resistant to erlotinib. Both cetuximab and huEGFR-7R antibody could only inhibit up to 35% of tumor growth at 3E-8 M concentration (FIG. 13B). In contrast, huEGFR-7R-SMCC-DM1 almost completely killed the tumor cells with EC50 of 3.2E-11 M. This data suggests that huEGFR-7R-SMCC-DM1 conjugate is highly effective against an NSCLC adenocarcinoma that is ALK inhibitor-resistant EML4-ALK+ H2228 cell line.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of treating cancer in a human patient comprising administering an amount of an epidermal growth factor receptor (EGFR) antibody immunoconjugate to a human patient with a tumor comprising tumor cells that are resistant or refractory to an EGFR antibody therapy, effective to inhibit growth of the tumor;
wherein the immunoconjugate has the formula (A)-(L)-(C), wherein:
(A) is an antibody or antigen binding fragment thereof that specifically binds EGFR and comprises the heavy chain variable region of SEQ ID NO:1 and the light chain variable region of SEQ ID NO:2 or SEQ ID NO:3;
(L) is a linker; and
(C) is a maytansinoid or maytansinoid analog; and
wherein said linker (L) links (A) to (C).

2. The method of claim 1, wherein the cancer is a squamous cell cancer, lung cancer, head and neck cancer, or an EGFR-positive cancer.

3. The method of claim 2, wherein the cancer is a squamous cell cancer.

4. The method of claim 2, wherein the cancer is lung cancer.

5. The method of claim 2, wherein the cancer is head and neck cancer.

6. The method of claim 2, wherein the cancer is an EGFR-positive cancer.

7. The method of claim 1, wherein at least one of the tumor cells: (1) contains one or more mutations in an EGFR-encoding gene; (2) contains one or more mutations in a PIK3CA, RAS, or PTEN encoding gene; (3) has an activated MET pathway; (4) has mesenchymal histology or has undergone epithelial-mesenchymal transition; or (5) has ERBB2 gene amplification or increased production of HER2 protein.

8. The method of claim 7, wherein the at least one of the tumor cells contains one or more mutations in an EGFR-encoding gene.

9. The method of claim 8, wherein the Mutated EGFR gene comprises a EGFRvIII mutation.

10. The method of claim 7, wherein the at least one of the tumor cells contains one or more mutations in a PIK3CA, RAS, or PTEN encoding gene.

11. The method of claim 7, wherein the at least one of the tumor cells has an activated MET pathway.

12. The method of claim 11, wherein said MET pathway activation is caused by MET gene amplification.

13. The method of claim 7, wherein the at least one of the tumor cells has mesenchymal histology or has undergone epithelial-mesenchymal transition.

14. The method of claim 7, wherein the at least one of the tumor cells has ERBB2 gene amplification.

15. The method of claim 7, wherein the at least one of the tumor cells has increased production of HER2 protein.

16. The method of claim 1, wherein the EGFR antibody therapy to which the cells are resistant or refractory is selected from the group consisting of: cetuximab, panitumumab, zalutumumab, necitumumab, and nimotuzumab.

17. The method of claim 1, wherein the human patient previously failed or is currently failing an EGFR therapy comprising administration of an EGFR antibody.

18. The method of claim 17, wherein the EGFR antibody is cetuximab.

19. The method of claim 17, wherein the EGFR antibody is panitumumab.

20. The method of claim 1, wherein the linker is selected from the group consisting of a cleavable linker, a non-cleavable linker, a hydrophilic linker, and a dicarboxylic acid based linker.

21. The method of claim 20, wherein the linker is a non-cleavable linker.

22. The method of claim 1, wherein the linker is selected from the group consisting of: N-succinimidyl 4-(2-pyridyldithio)pentanoate (SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl)cyclohexanecarboxylate (SMCC); N-sulfosuccinimidyl 4-(maleimidomethyl)cyclohexanecarboxylate (sulfo SMCC); N-succinimidyl-4-(iodoacetyl)-aminobenzoate (SIAB); N-succinimidyl-[(N-maleimidopropionamido)-tetraethyleneglycol]ester (NHS-PEG4-maleimide); N-(beta-maleimidopropyloxy)succinimide ester (BMPS); and gamma-maleimidobutyric acid N-succinimidyl ester (GMBS).

23. The method of claim 1, wherein the cytotoxic agent is a maytansinoid analog.

24. The method of claim 1, wherein the cytotoxic agent is a maytansinoid.

25. The method of claim 24, wherein the cytotoxic agent is N(2')-deacetyl-N(2')-(3-mercapto-1-oxopropyl)-maytansine (DM1) or N(2')-deacetyl-N2'-(4-mercapto-4-methyl-1-oxopentyl)-maytansine (DM4).

26. The method of claim 1, wherein the EGFR antibody immunoconjugate comprises the linker SMCC and the maytansinoid DM1.

27. The method of claim 1, wherein the EGFR antibody immunoconjugate is administered with an additional anti-neoplastic agent.

28. The method of claim 27, wherein the EGFR antibody immunoconjugate is administered simultaneously with the anti-neoplastic agent.

29. The method of claim 27, wherein the EGFR antibody immunoconjugate and anti-neoplastic agent are administered in any temporal order.

30. The method of claim 16, wherein the EGFR therapy to which the cells are resistant or refractory is panitumumab.

31. The method of claim 16, wherein the EGFR therapy to which the cells are resistant or refractory is zalutumumab.

32. The method of claim 16, wherein the EGFR therapy to which the cells are resistant or refractory is necitumumab.

33. The method of claim 16, wherein the EGFR therapy to Which the cells are resistant or refractory is nimotuzumab.

34. The method of claim 16, wherein the EGFR therapy to which the cells are resistant or refractory is cetuximab.

35. The method of claim 17, wherein the EGFR antibody is zalutumumab.

36. The method of claim 17, wherein the EGFR antibody is necitumumab.

37. The method of claim 17, wherein the EGFR antibody is nimotuzumab.

38. A method of treating cancer in a human patient comprising administering an amount of an epidermal growth factor receptor (EGFR) antibody immunoconjugate to a human patient with a tumor comprising tumor cells that are resistant or refractory to an EGFR antibody therapy, effective to inhibit growth of the tumor;
  wherein the immunoconjugate has the formula (A)-(L)-(C), wherein:
  (A) is an antibody or antigen binding fragment thereof that specifically binds EGFR and comprises the heavy chain variable region of SEQ ID NO: 1 and the light chain variable region of SEQ ID NO:2 or SEQ ID NO:3;
  (L) is a non-cleavable linker; and
  (C) is a cytotoxic agent; and wherein said linker (L) links (A) to (C).

39. The method of claim 38, wherein the cancer is a squamous cell cancer, lung cancer, head and neck cancer, or an EGFR-positive cancer.

40. The method of claim 38, wherein at least one of the tumor cells: (1) contains one or more mutations in an EGFR-encoding gene; (2) contains one or more mutations in a PIK3CA, RAS, or PTEN encoding gene; (3) has an activated MET or IGF1R pathway; (4) has mesenchymal histology or has undergone epithelial-mesenchymal transition; or (5) has ERBB2 gene amplification or increased production of HER2 protein.

41. The method of claim 40, wherein the mutated EGFR gene comprises a EGFRvIII mutation.

42. The method of claim 40, wherein the at least one of the tumor cells has an activated MET pathway, and wherein said MET pathway activation is caused by MET gene amplification.

43. The method of claim 38, wherein the EGFR antibody therapy to which the cells are resistant or refractory is selected from the group consisting of: cetuximab, panitumumab, zalutumumab, necitumumab, and nimotuzumab.

44. The method of claim 38, wherein the human patient previously failed or is currently failing an EGFR therapy comprising administration of an EGFR antibody selected from the group consisting of: cetuximab, panitumumab, zalutumumab, necitumumab, and nimotuzumab.

45. The method of claim 38, wherein the linker is selected from the group consisting: SMCC, sulfoSMCC, NHS-PEG4-maleimide, BMPS, and GMBS.

46. The method of claim 45, wherein the non-cleavable linker is SMCC.

47. The method of claim 38, wherein the cytotoxic agent is selected from the group consisting of: a maytansinoid, maytansinoid analog, doxorubicin, a modified doxorubicin, benzodiazepine, taxoid, CC-1065, CC-1065 analog, duocarmycin, duocarmycin analog, calicheamicin, dolastatin, dolastatin analog, auristatin, tomaymycin derivative, and leptomycin derivative or a prodrug of the agent.

48. The method of claim 47, wherein the cytotoxic agent is a maytansinoid.

49. The method of claim 48, wherein the cytotoxic agent is DM1 or DM4.

50. The method of claim 38, wherein the EGFR antibody immunoconjugate comprises the linker SMCC and the maytansinoid DM1.

51. The method of claim 38, wherein the EGFR antibody immunoconjugate is administered with an additional anti-neoplastic agent.

* * * * *

UNITED STATES PATENT AND TRADEMARK OFFICE
CERTIFICATE OF CORRECTION

PATENT NO. : 9,233,171 B2
APPLICATION NO. : 13/682948
DATED : January 12, 2016
INVENTOR(S) : Setiady et al.

It is certified that error appears in the above-identified patent and that said Letters Patent is hereby corrected as shown below:

Claims

At column 38, line 50 (Claim 9), please replace "Mutated" with --mutated--

At column 40, line 43 (Claim 45), please replace "consisting:" with --consisting of:--

Signed and Sealed this
Nineteenth Day of April, 2016

Michelle K. Lee
*Director of the United States Patent and Trademark Office*